(12) United States Patent
Jockel et al.

(10) Patent No.: US 11,612,710 B2
(45) Date of Patent: Mar. 28, 2023

(54) ENDOTRACHEAL TUBE HOLDING DEVICE

(71) Applicant: Hollister Incorporated, Libertyville, IL (US)

(72) Inventors: Mark W. Jockel, Chicago, IL (US); Gregory J. Czaplewski, Glendale Heights, IL (US); Anthony Scalise, Plainfield, IL (US); Tze Wan Chung, Fox River Grove, IL (US); Peter L. Visconti, Gurnee, IL (US); Christina Augustyn, Chicago, IL (US); Rebecca E. Merryman, Libertyville, IL (US); Thai H. Dang, Gurnee, IL (US); Patrick C. Tetzlaff, Caledonia, WI (US); Brian T. Leadingham, Pleasant Prairie, WI (US)

(73) Assignee: Hollister Incorporated, Libertyville, IL (US)

( * ) Notice: Subject to any disclaimer, the term of this patent is extended or adjusted under 35 U.S.C. 154(b) by 871 days.

(21) Appl. No.: 16/341,604

(22) PCT Filed: Oct. 13, 2017

(86) PCT No.: PCT/US2017/056567
§ 371 (c)(1),
(2) Date: Apr. 12, 2019

(87) PCT Pub. No.: WO2018/071804
PCT Pub. Date: Apr. 19, 2018

(65) Prior Publication Data
US 2020/0222651 A1 Jul. 16, 2020

Related U.S. Application Data

(60) Provisional application No. 62/407,722, filed on Oct. 13, 2016, provisional application No. 62/480,889, filed on Apr. 3, 2017.

(51) Int. Cl.
*A61M 16/04* (2006.01)
*A61M 16/06* (2006.01)
*A61M 25/02* (2006.01)

(52) U.S. Cl.
CPC .... *A61M 16/0497* (2013.01); *A61M 16/0493* (2014.02); *A61M 16/0683* (2013.01);
(Continued)

(58) Field of Classification Search
CPC ............ A61M 16/0488; A61M 16/049; A61M 16/0493; A61M 16/0497
See application file for complete search history.

(56) References Cited

U.S. PATENT DOCUMENTS 3,946,742 A 3/1976 Eross
4,069,820 A 1/1978 Berman
(Continued)

FOREIGN PATENT DOCUMENTS

EP 1525021 B1 11/2006
EP 2015814 B1 7/2015
(Continued)

OTHER PUBLICATIONS

Extended European Search Report from European Patent App. No. EP21151394, dated Apr. 30, 2021.
(Continued)

*Primary Examiner* — LaToya M Louis
(74) *Attorney, Agent, or Firm* — Cook Alex Ltd.

(57) ABSTRACT

Endotracheal tube holders having bottom surface including protrusions that contact the endotracheal tube, and a strap that wraps around the bottom surface and the tube to secure the endotracheal tube to the tube holder.

17 Claims, 16 Drawing Sheets

(52) U.S. Cl.
CPC . *A61M 2025/022* (2013.01); *A61M 2025/024* (2013.01); *A61M 2209/088* (2013.01)

(56) References Cited

U.S. PATENT DOCUMENTS

| | | | |
|---|---|---|---|
| 4,331,144 A | | 5/1982 | Wapner |
| 4,351,331 A | | 9/1982 | Gereg |
| 4,449,527 A | | 5/1984 | Hinton |
| 4,681,094 A | | 7/1987 | Rolnick |
| 4,906,234 A | | 3/1990 | Voychehovski |
| 5,295,480 A | * | 3/1994 | Zemo ............. A61M 16/0488 128/207.17 |
| 5,345,931 A | | 9/1994 | Battaglia, Jr. |
| 5,419,319 A | | 5/1995 | Werner |
| 5,437,273 A | | 8/1995 | Bates |
| 5,443,060 A | | 8/1995 | Visveshwara |
| 5,490,504 A | | 2/1996 | Vrona |
| 5,555,881 A | | 9/1996 | Rogers |
| 5,653,232 A | | 8/1997 | Rogers |
| 5,718,225 A | | 2/1998 | Visveshwara |
| 6,067,985 A | | 5/2000 | Islava |
| 6,318,765 B1 | | 11/2001 | Slais |
| 6,526,978 B2 | | 3/2003 | Dominguez |
| 6,578,576 B1 | | 6/2003 | Taormina |
| 6,722,369 B1 | | 4/2004 | Kron |
| 6,755,191 B2 | | 6/2004 | Bertoch |
| 7,063,088 B1 | | 6/2006 | Christopher |
| 7,624,735 B2 | | 12/2009 | Ho |
| 7,766,008 B2 | | 8/2010 | Manishen |
| 8,028,704 B2 | | 10/2011 | Reynolds, II |
| 8,096,300 B2 | | 1/2012 | Russo |
| 8,256,427 B2 | | 9/2012 | Chang |
| 8,302,597 B2 | | 11/2012 | Beely |
| 8,360,063 B2 | | 1/2013 | Liland |
| 8,460,248 B2 | | 6/2013 | Ryan |
| 8,636,008 B2 | | 1/2014 | Flory |
| 8,656,925 B2 | | 2/2014 | Davis |
| 8,726,903 B2 | | 5/2014 | Levine |
| 8,974,382 B2 | | 3/2015 | Taljaard |
| 8,978,656 B2 | | 3/2015 | Chien |
| 9,233,221 B2 | | 1/2016 | Haider |
| 9,308,340 B2 | | 4/2016 | Bond |
| 9,358,367 B2 | | 6/2016 | Velez-Rivera |
| 9,629,972 B1 | | 4/2017 | Vu |
| 9,707,364 B2 | | 7/2017 | Islava |
| 9,713,691 B2 | | 7/2017 | Kirn |
| 9,814,853 B2 | | 11/2017 | Kanowitz |
| 9,833,586 B2 | | 12/2017 | Yokota |
| 9,833,588 B2 | | 12/2017 | Fuller |
| 9,981,101 B2 | | 5/2018 | Vanmiddendorp |
| 10,195,387 B2 | | 2/2019 | Gulliver |
| 2005/0092328 A1 | | 5/2005 | Herrick |
| 2005/0133038 A1 | | 6/2005 | Rutter |
| 2006/0081245 A1 | | 4/2006 | Gould |
| 2006/0127031 A1 | | 11/2006 | Ho |
| 2009/0084377 A1 | | 4/2009 | Hajgato |
| 2009/0211573 A1 | | 8/2009 | Russo |
| 2009/0255538 A1 | | 10/2009 | Thomson |
| 2011/0126839 A1 | | 6/2011 | Levine |
| 2011/0180065 A1 | | 7/2011 | Hajgato |
| 2011/0240034 A1 | | 10/2011 | Ciccone |
| 2012/0168571 A1 | | 7/2012 | Bond |
| 2013/0061853 A1 | | 3/2013 | De Lulio |
| 2013/0068233 A1 | | 3/2013 | De Lulio |
| 2013/0146068 A1 | | 6/2013 | Van Wagenen |
| 2013/0146069 A1 | | 6/2013 | Van Wagenen |
| 2013/0168507 A1 | | 7/2013 | Eastman |
| 2013/0327337 A1 | | 12/2013 | Devapatla |
| 2014/0238406 A1 | | 8/2014 | Borre |
| 2014/0144656 A1 | | 9/2014 | Visconti |
| 2014/0261441 A1 | | 9/2014 | Phillips |
| 2014/0261462 A1 | | 9/2014 | Visconti |
| 2014/0261463 A1 | | 9/2014 | Visconti |
| 2015/0141942 A1 | | 5/2015 | Garrett |
| 2015/0190599 A1 | | 7/2015 | Colman |
| 2016/0095995 A1 | | 4/2016 | Haider |
| 2016/0121067 A1 | | 5/2016 | Vanmiddendorp |
| 2016/0235934 A1 | | 8/2016 | Poulsen |
| 2016/0235935 A1 | | 8/2016 | Mirza |
| 2016/0271349 A1 | | 9/2016 | Zickefoose |
| 2016/0361509 A1 | | 12/2016 | Blessing, Jr. |
| 2017/0197049 A1 | | 7/2017 | Doll |
| 2017/0209300 A1 | | 7/2017 | Radmand |
| 2018/0071556 A1 | | 3/2018 | Hung |
| 2019/0070378 A1 | | 3/2019 | Kanowitz |

FOREIGN PATENT DOCUMENTS

| | | |
|---|---|---|
| EP | 3210643 A1 | 8/2017 |
| EP | 2582422 B1 | 10/2018 |
| EP | 3052171 B1 | 12/2018 |
| EP | 3461524 A1 | 4/2019 |
| WO | WO 95/29727 A1 | 11/1995 |
| WO | WO 1997/031669 | 9/1997 |
| WO | WO 1997/048432 | 12/1997 |
| WO | WO 2004/052267 | 6/2004 |
| WO | WO 2006/060821 | 6/2006 |
| WO | WO 2006/127031 | 11/2006 |
| WO | WO 2008/151180 | 12/2008 |
| WO | WO 2009/066277 | 5/2009 |
| WO | WO 2010/033109 | 3/2010 |
| WO | WO 2011/066557 | 6/2011 |
| WO | WO 2012/064732 | 5/2012 |
| WO | WO 2013/040230 A1 | 3/2013 |
| WO | WO 2014/144656 A1 | 9/2014 |
| WO | WO 2014/145694 | 9/2014 |
| WO | WO 2014/186297 | 11/2014 |
| WO | WO 2015/073279 | 5/2015 |
| WO | WO 2015/127443 | 8/2015 |
| WO | WO 2017/129935 | 8/2017 |
| WO | WO 2017/179780 | 10/2017 |
| WO | WO 2018/067997 | 4/2018 |
| WO | WO 2018/091753 | 5/2018 |

OTHER PUBLICATIONS

International Search Report and Written Opinion dated Apr. 11, 2018, for International Application No. PCT/US2017/056567.
Coopersurgical, NEO-fit, product brochure, dated 2012.

\* cited by examiner

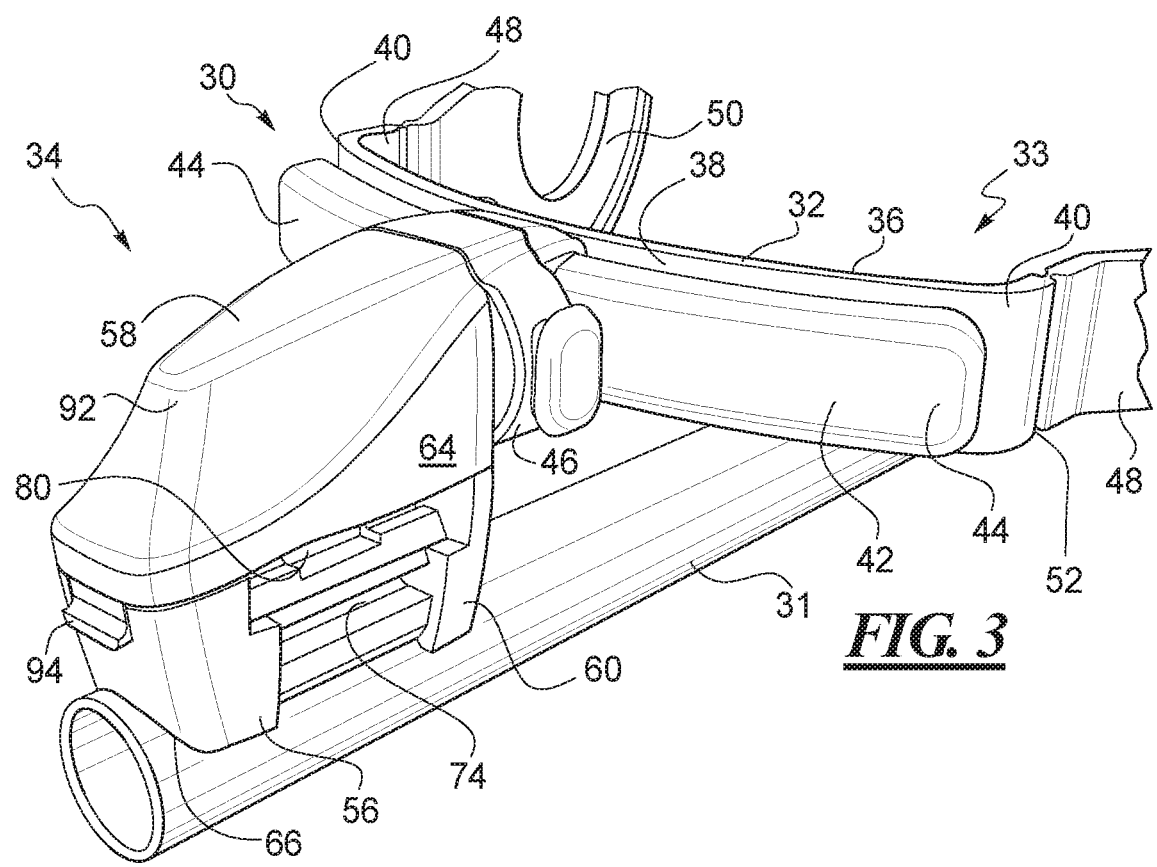
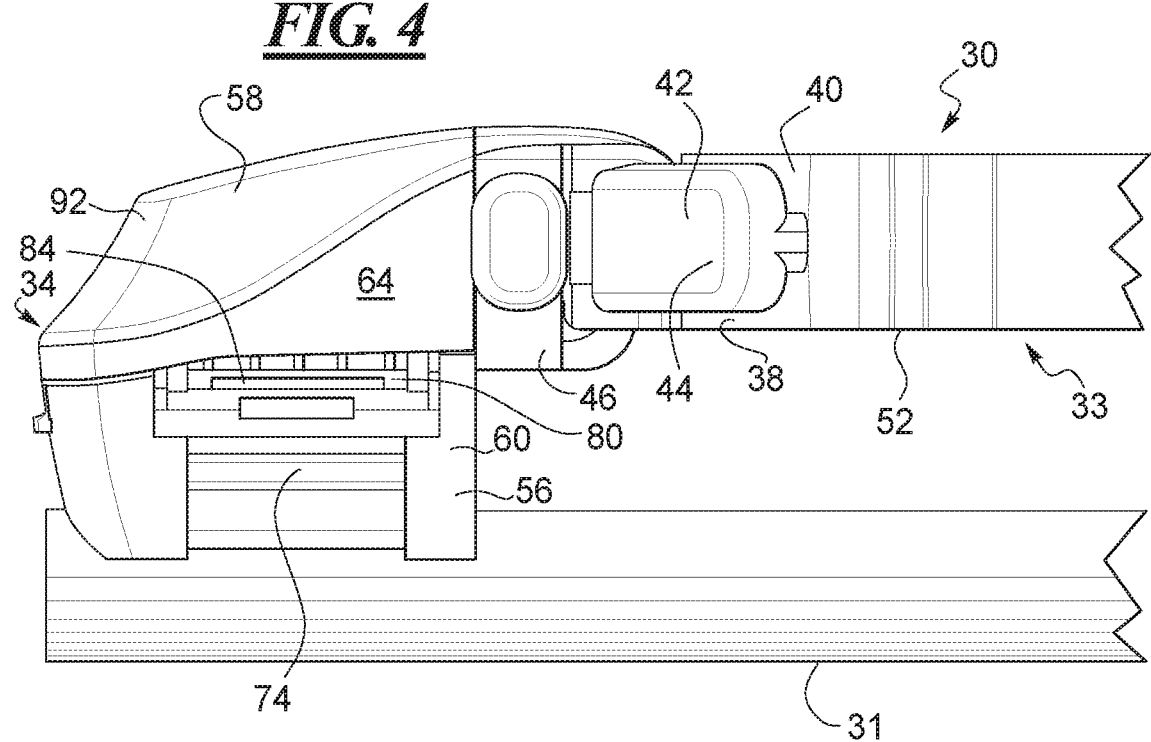

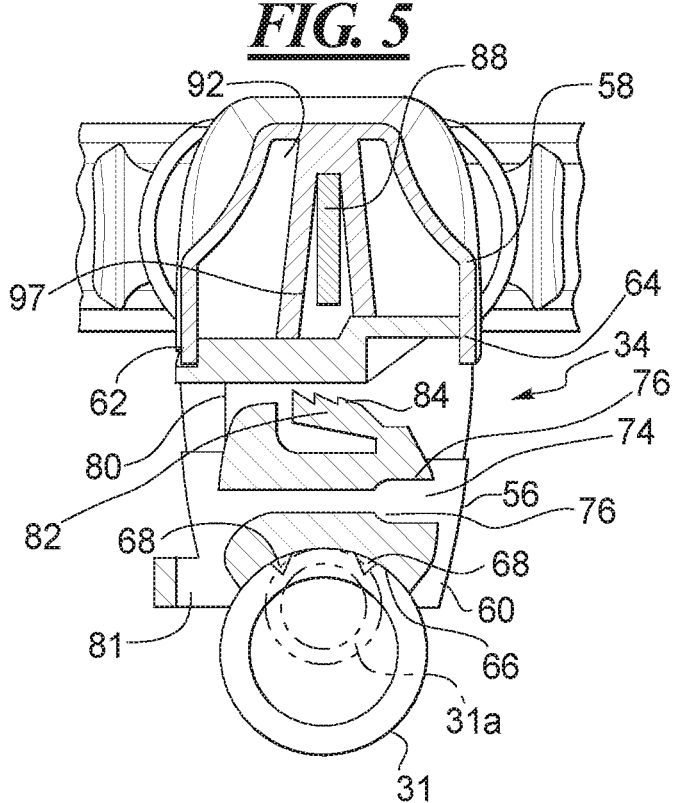
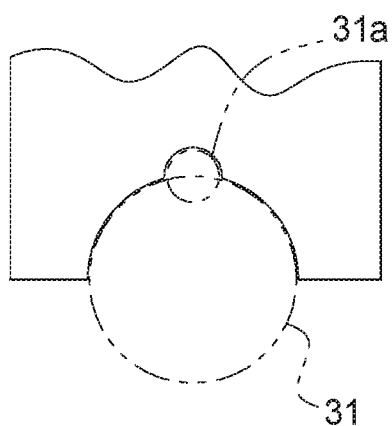
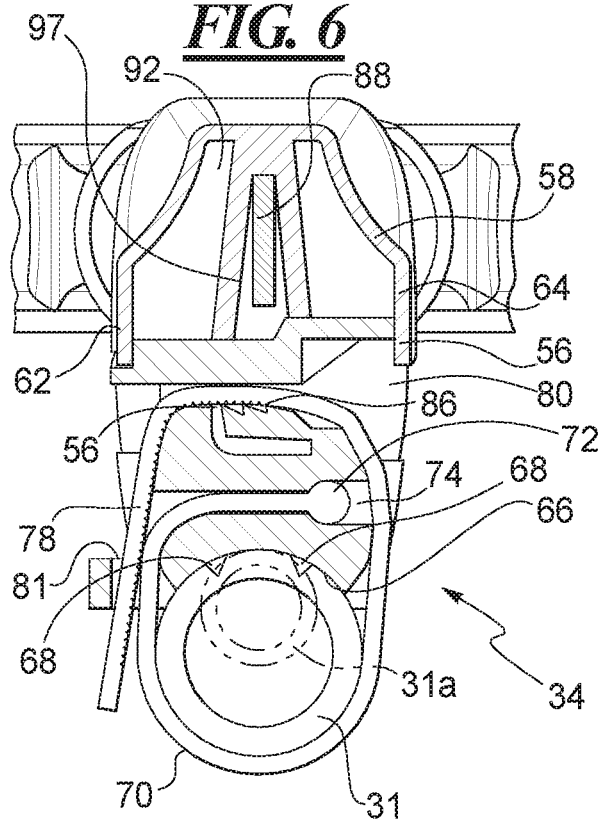
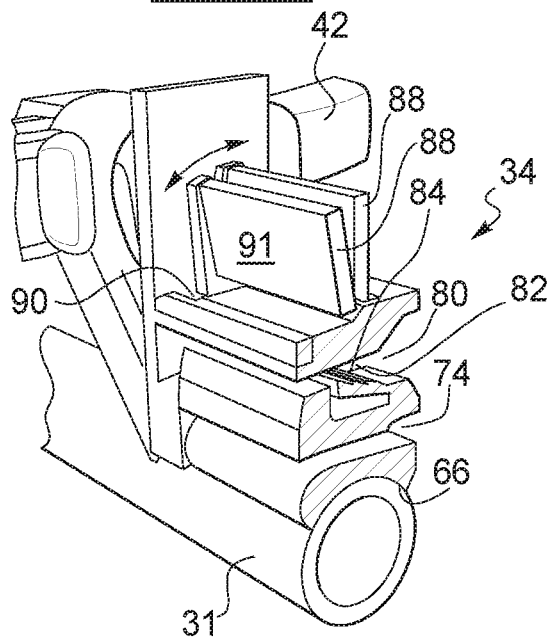

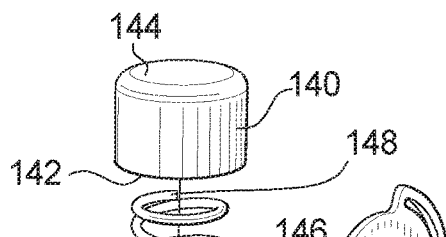
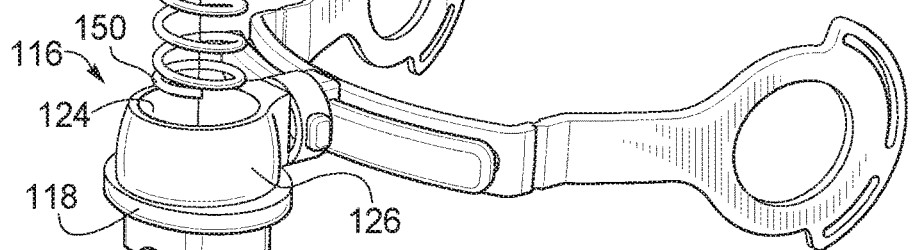
FIG. 15
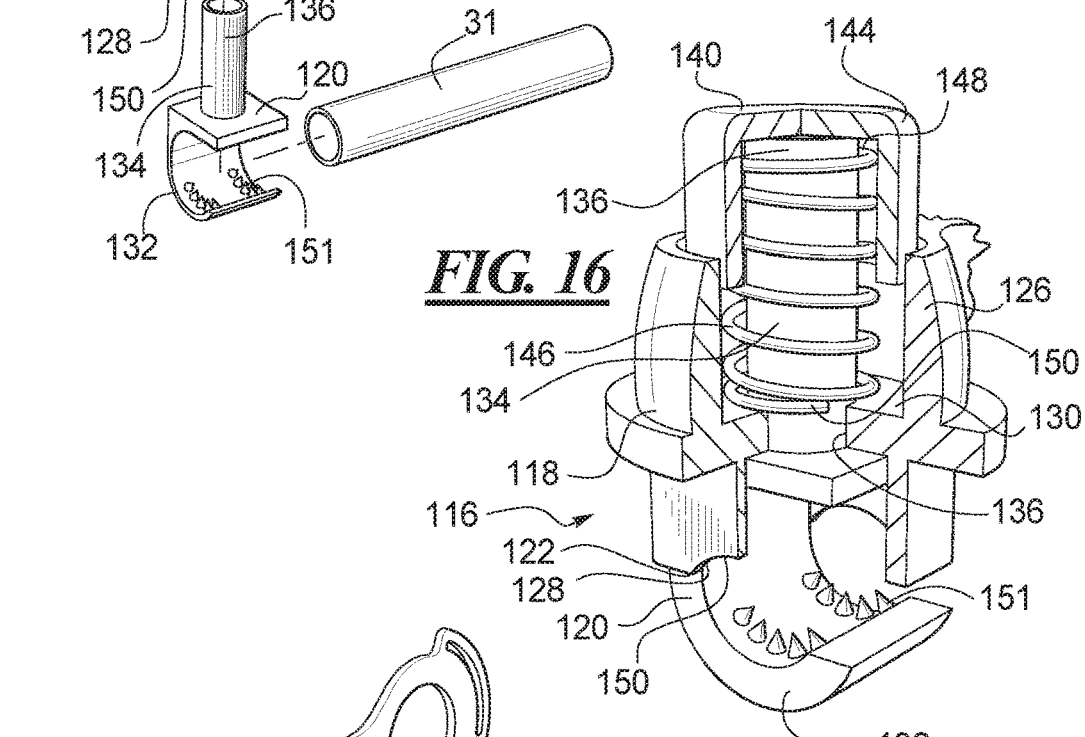
FIG. 16
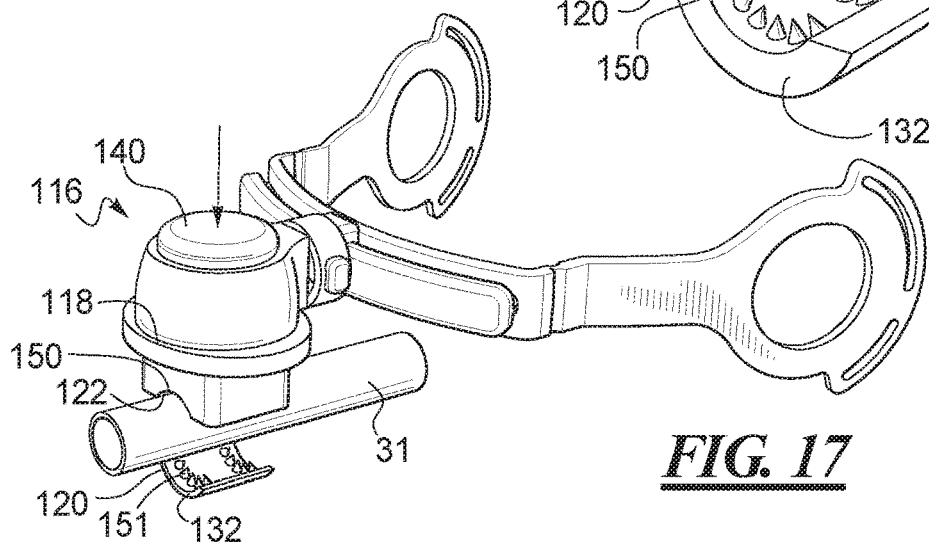
FIG. 17

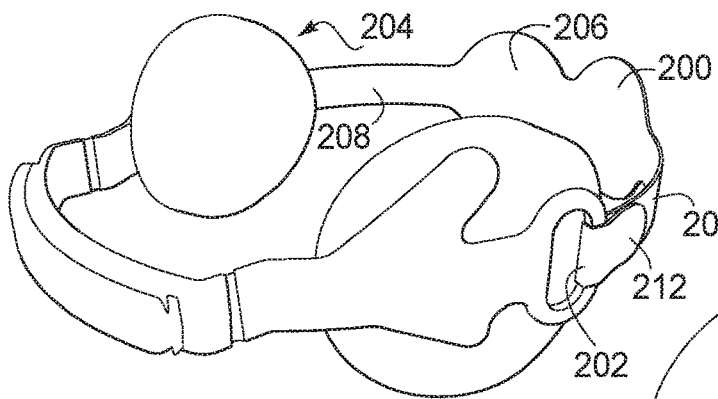
FIG. 28
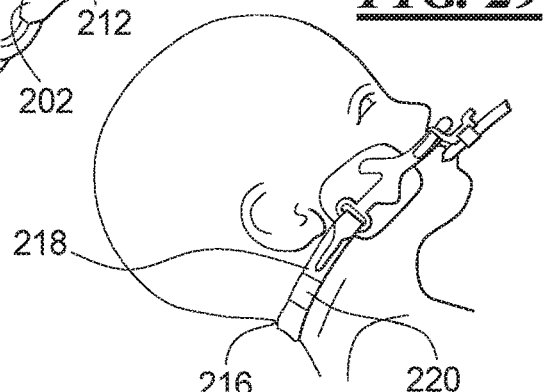
FIG. 29
FIG. 30
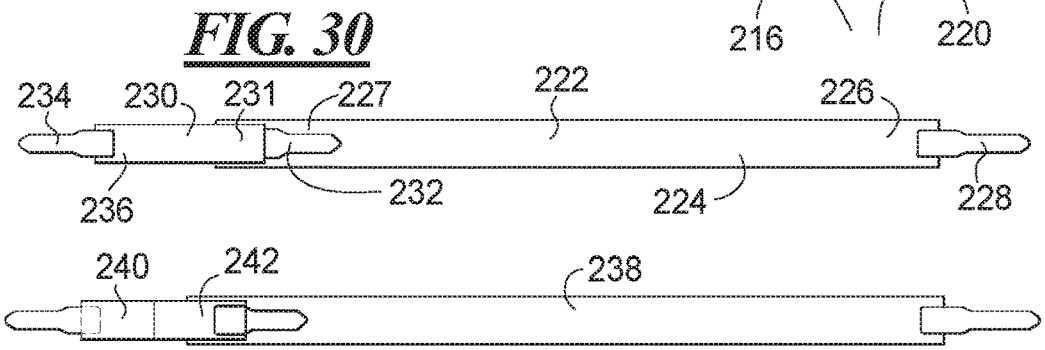
FIG. 31
FIG. 32

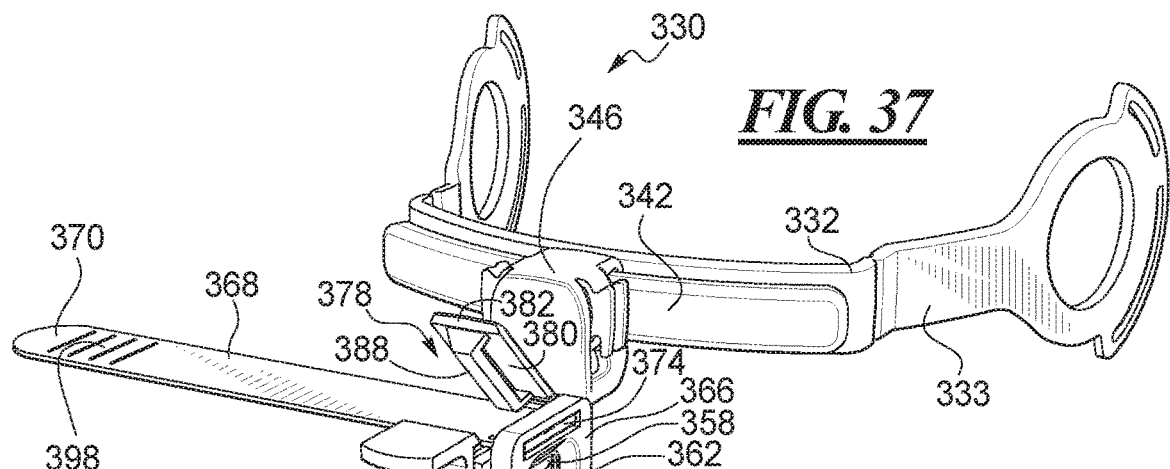
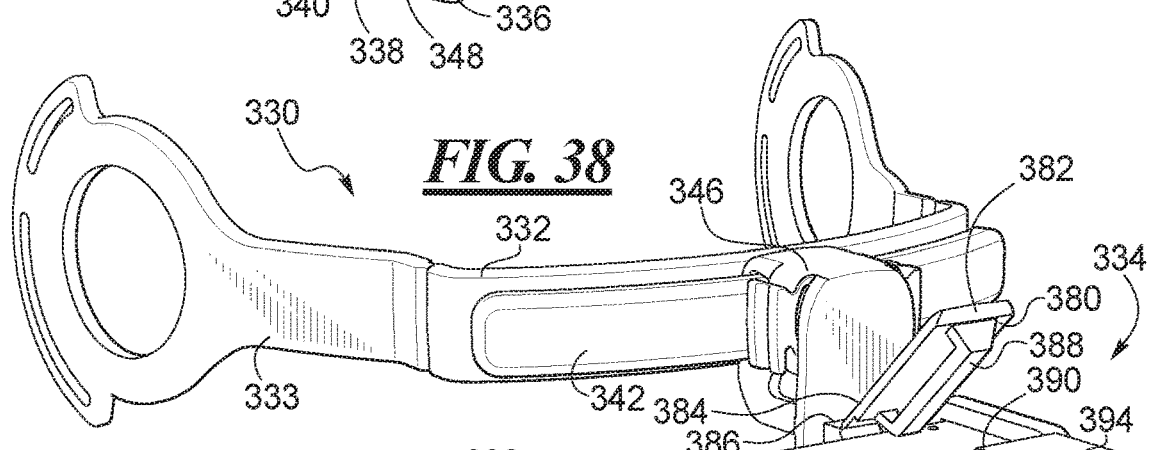
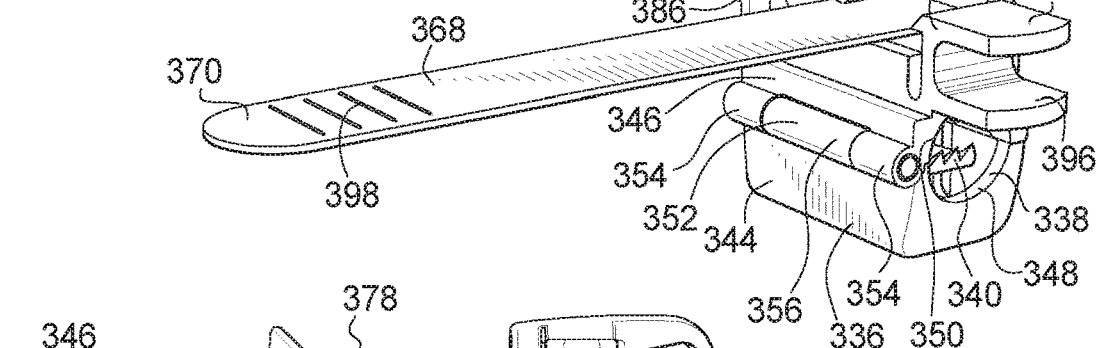
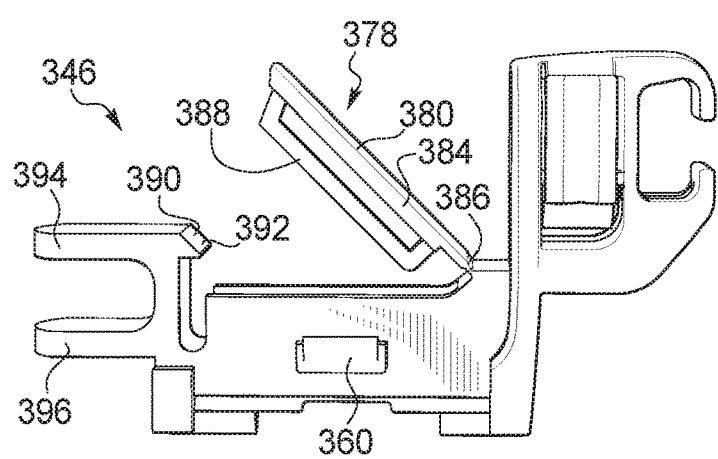

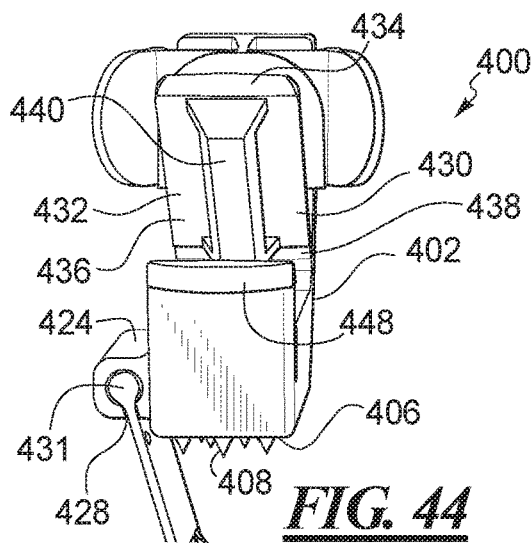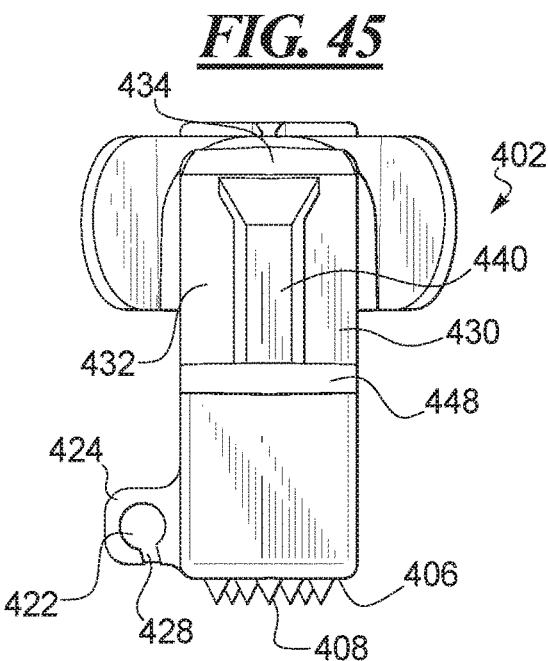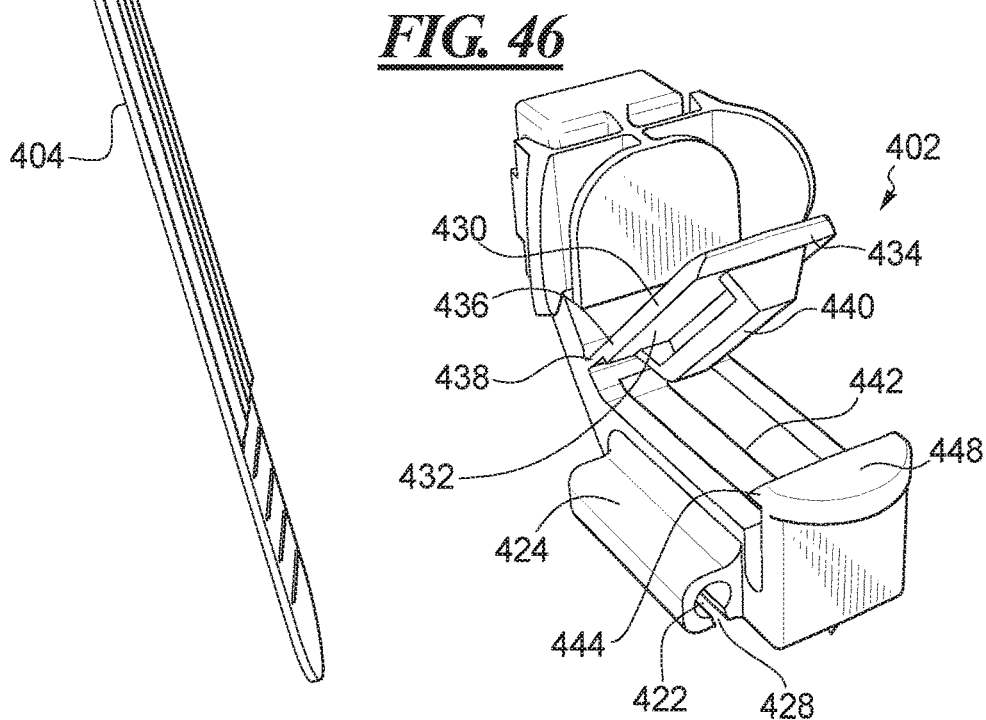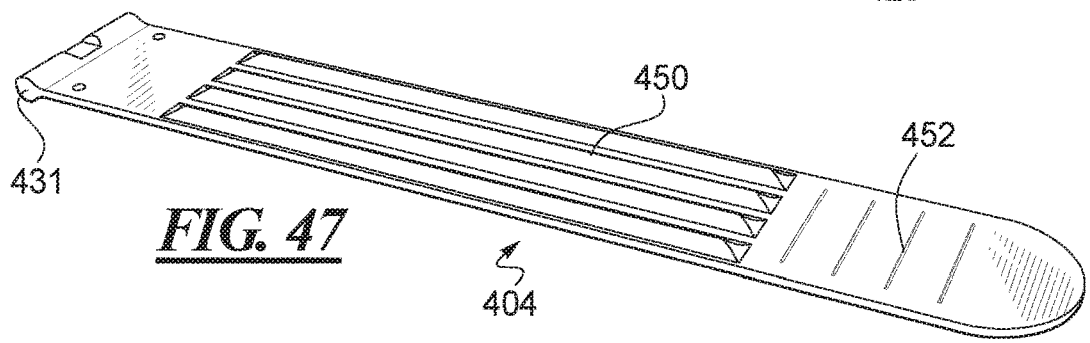

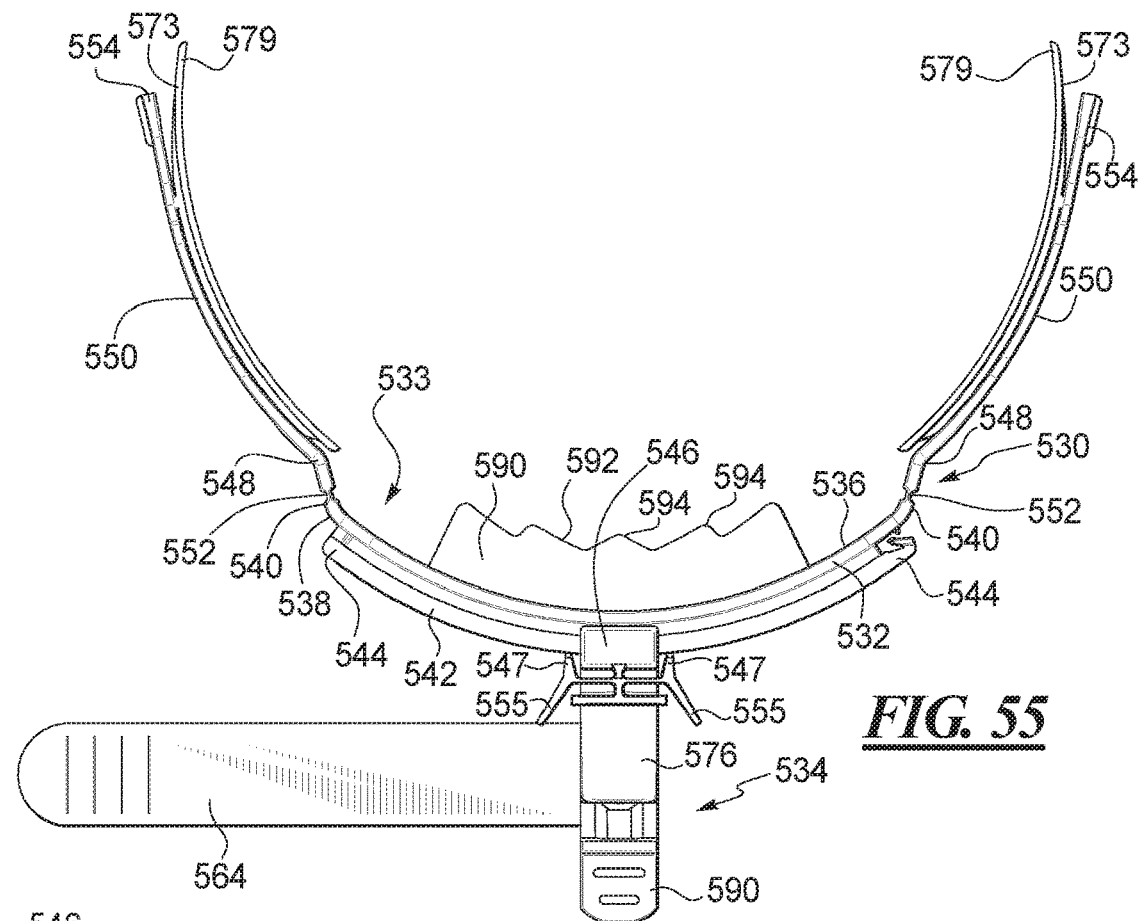
FIG. 55
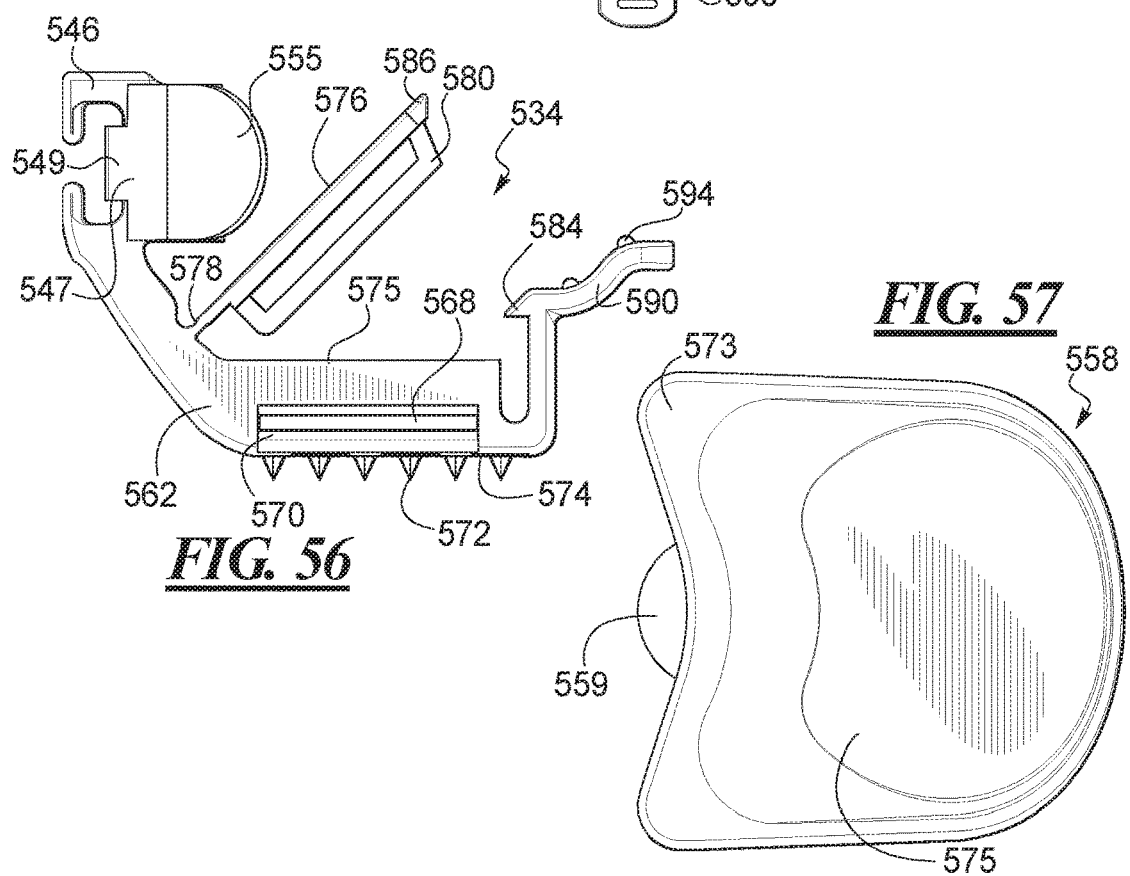
FIG. 56
FIG. 57

ENDOTRACHEAL TUBE HOLDING DEVICE

The present application is the U.S. National Stage Application of PCT Application No. PCT/US2017/056567, filed October 13, 2017, which claims the benefit of and priority to U.S. Provisional Patent Application Ser. No. 62/407,722, filed Oct. 13, 2016, and U.S. Provisional Patent Application Ser. No. 62/480,889, filed Apr. 3, 2017, all of which are incorporated herein by reference

FIELD OF DISCLOSURE

The present disclosure is generally directed to medical tube devices, and more particularly to devices for holding an endotracheal tube on a patient.

BACKGROUND

Endotracheal (ET) tubes are commonly inserted through the mouth and into the trachea of patients under critical care. The ET tube is used to maintain an open airway for the patient to breath and to allow mechanical assistance of breathing. ET tubes are often inserted prior to surgery or are used on trauma or critically ill patients that may require intubation for extended periods of time. Many instances in which a patient is intubated require that the tube remain in place for approximately 48 to 72 hours and, in some circumstances, the period of use may be extended for 7 to 14 days or more days.

There are several known methods and devices for securing an ET tube on a patient. One such device is manufactured and sold by Hollister, Inc. (the assignee of the present patent) under the trademark AnchorFast®. The AnchorFast® has a frame that may be secured to a patient using adhesive cheek pads and may include a head/neck strap that encircles the back of the patients head/neck. The frame includes a central support beam and cheek plates having cheek pads that are skin friendly and that have adhesive patches to help retain the frame in the proper position on the patient's face during use. A tube holder is side-to-side adjustable on the beam and is used to secure an ET tube to the device.

Earlier versions of AnchorFast ET tube holders are disclosed in U.S. Pat. No. 5,490,504 and US Pub. Pat. Application No. 2014/0261462, both of which are assigned to Hollister, Inc. and both of which are incorporated by reference herein. The '504 patent and '462 application both disclose devices that have a central support beam and a tube holder, including side-to-side adjustability of the tube holder and ET tube secured thereto. However, the '504 patent does not include the cheek pads and cheek plates.

One problem with current ET tube holding devices is that such devices may have some difficultly securing and holding smaller sized ET tubes, such as those used for pediatric and petite patients. In a typical adult patient medical setting, one advantage provided by ET tube holders is that they hold the ET tube in place after the medical professional has placed the ET tube into the desired position within the patient's trachea. That is, the ET tube holder aids in preventing accidental or undesired movement of the ET tube by the patient or the medical professional. However, because the current ET tube holders may have some difficulty with securing smaller sized tubes, many medical professionals will often choose to simply use medical tape applied to the patient's skin to secure such smaller ET tubes in pediatric and smaller adult patient applications. Taping the ET tube in pediatric applications may not be the most desirable option because children oftentimes do not understand medical treatments and may attempt to move or remove an ET tube if they become panicked or are feeling discomfort.

Accordingly, there remains a need for ET tube holding devices that can secure medical tubes of various sizes, and especially ET tube holding devices that can secure smaller sized tubes that may be used in pediatric applications and applications involving petite individuals.

SUMMARY

The present disclosure discloses various features of tube holding devices.

In one aspect, a device for holding an endotracheal tube to a patient includes a support configured to fit adjacent to a patient's mouth and a tube holder configured to hold an endotracheal tube wherein the tube holder is coupled to the support. The tube holder includes a body having opposed sides and a bottom side wherein the bottom side has a plurality of shark-tooth shaped protrusions for contacting an endotracheal tube. The device further includes an elongated, flexible strap extending from one side of the body and having a free length adapted to be wrapped around the bottom side of the body and the endotracheal tube to secure the endotracheal tube to the bottom side of the body.

In another aspect, a tube holder includes a bottom surface configured to contact an endotracheal tube and a strap configured to secure the tube against the bottom surface. The tube holder further including a clamping mechanism wherein the clamping mechanism includes a lever for clamping and securing the strap in position and a catch for locking the lever in position. A release tab to move the catch wherein the release tab has stepped configuration. For example, the release tab may have an S-shape or Z-shape configuration.

In one aspect, a device for holding an endotracheal tube to a patient wherein the device includes an elongated support configured to fit adjacent to a patient's mouth. The elongated support having an inner side facing the patient's face, an exposed side opposite the inner side, a top side and a bottom side opposite the top side. The bottom side including a plurality catches laterally spaced apart along one or both of the bottom side and the top side. The device further including a tube holder configured to hold an endotracheal tube and a positioning member slidably mounted to the elongated support and coupling the tube holder to the elongated support. The positioning member is selectively laterally repositionable along the elongated support so as to reposition the tube holder relative thereto. The positioning member being releasably lockable in position relative to the elongated support wherein the positioning member includes a post having a locked position and an unlocked position. In the locked position the post engages one or more of the catches on the bottom and/or top side of the elongated support to lock the positioning member in position, and in the unlocked position, the post disengaging the catches on the bottom and/or top side of the elongated support to allow the positioning member to be repositioned along the track.

In another aspect, a device for holding an endotracheal tube to a patient wherein the device includes a support configured to fit adjacent to a patient's mouth and a tube holder configured to hold an endotracheal tube wherein the tube holder is coupled to the support. The tube holder includes a body having opposed sides and a bottom side. The bottom side having a generally arcuate surface being adapted to receive an endotracheal tube. The device also includes an elongated flexible strap extending from one side of the body and having a free length adapted to be wrapped around the bottom side of the body and the endotracheal tube to secure the endotracheal tube to the bottom side of the body. The other side of the body having an opening for receiving the free length into a clamping member for securing the free length of the elongated flexible strap.

In yet another aspect, a device for holding an endotracheal tube to a patient wherein the device includes a support configured to fit adjacent to a patient's mouth and a tube holder configured to hold an endotracheal tube wherein the tube holder is coupled to the support. The tube holder including a housing having a top end and a bottom end. The holder also including a carriage having an upper portion extending within the housing and a lower portion movable relative the bottom end of the housing. The lower portion of the carriage being movable away from the bottom end of the housing to define a space therebetween which is configured to accept an endotracheal tube. The lower portion of the carriage also being movable toward the bottom end of the housing to clamp the endotracheal tube therebetween. The device also including an actuator operatively connected to the carriage which moves the carriage relative to the housing.

In yet a further aspect, a device for holding an endotracheal tube to a patient wherein the device includes a support configured to fit adjacent to a patient's mouth and a tube holder configured to hold an endotracheal tube wherein the tube holder is coupled to the support. The tube holder including a housing having a top portion and a bottom portion. The housing movable between an opened position or configuration wherein the top and bottom portions are at least partially separated from one another and a closed position or configuration wherein the top portion and the bottom portion are engaged with one another. In the closed position, the housing defining a passageway therethrough for accommodating an endotracheal tube. The holder also including a clamping member contained within the housing and configured to retain the endotracheal tube relative to the housing when the housing is in the closed position.

In yet another aspect, a device for holding an endotracheal tube to a patient wherein the device includes a frame having opposed ends adapted to be placed on either side of the patient's face and an endotracheal tube holder. The device also includes a two-piece strap for securing the frame to the patient's head. The two-piece strap being configured to encircle a patient's head or neck and to be connected to the opposed ends of the frame. The two-piece strap includes a first elongated segment having first and second end portions and a second elongated segment having first and second end portions. The first end portion of the first elongated segment being adapted to be adjustably connected to one end of the frame and the second end portion of the second elongated segment being adapted to being adjustably connected to the other end of the frame. The second end portion of the first elongated segment and the first end portion of the second elongated segment being releasable connected to each other to allow adjusting of the strap.

BRIEF DESCRIPTION OF THE DRAWINGS

FIG. 3 is a partial perspective view of the ET tube holding device shown in FIG. 1;

FIG. 4 is a partial side perspective view of the ET tube holding device shown in FIG. 1;

FIG. 4A is a front view of another embodiment of an ET holding device;

FIG. 5 is a cross-sectional view of the ET tube holding device shown in FIG. 1;

FIG. 6 is a cross-sectional view of the ET tube holding device shown in FIG. 1;

FIG. 7 is a perspective cut-away view of the ET tube holding device shown in FIG. 1;

FIG. 15 is a exploded perspective view of another embodiment of a tube holder in accordance with the present disclosure;

FIG. 16 is a partial cut-away view of tube holder shown in FIG. 15;

FIG. 17 is a perspective view of the tube holder of FIG. 15;

FIG. 28 is a perspective view of a prior art tube holder device;

FIG. 29 is a perspective view of a tube holder device showing one embodiment of a head/neck securing strap of the present disclosure;

FIG. 30 is a top plan view of another embodiment of a head/neck strap of the present disclosure;

FIG. 31 is a top plan view of another embodiment of a head/neck strap of the present disclosure;

FIG. 32 are perspective views of head/neck strap introduction members of the present disclosure;

FIG. 37 is a perspective view of another embodiment of an ET tube holding device of the present disclosure;

FIG. 38 is a perspective view of the ET tube holding device of FIG. 37;

FIG. 39 is a side perspective view of the top housing of the tube holder of the device shown in FIG. 37;

FIG. 44 is a perspective view of another embodiment of the an ET tube holding device of the present disclosure;

FIG. 45 is a front view of the tube holder of the device of FIG. 44;

FIG. 46 is a top perspective view of the tube holder of the device of FIG. 44;

FIG. 47 is a perspective view of a securement element of the tube holder of FIG. 44;

FIG. 55 is a top plan view of the ET tube holding device of FIG. 53;

FIG. 56 is a side elevation view of the tube holder of FIG. 53; and

FIG. 57 is a side elevation view of the cheek pad of FIG. 53.

DESCRIPTION OF THE PREFERRED EMBODIMENTS

While the devices of the present disclosure will be described in terms of certain preferred or alternative embodiments, it is contemplated that such devices may employ various structures, modifications and alternatives.

The disclosed ET tube holding devices solve or improve upon one or more of the above-noted and/or other problems and disadvantages with prior know holding devices.

Figure 1:
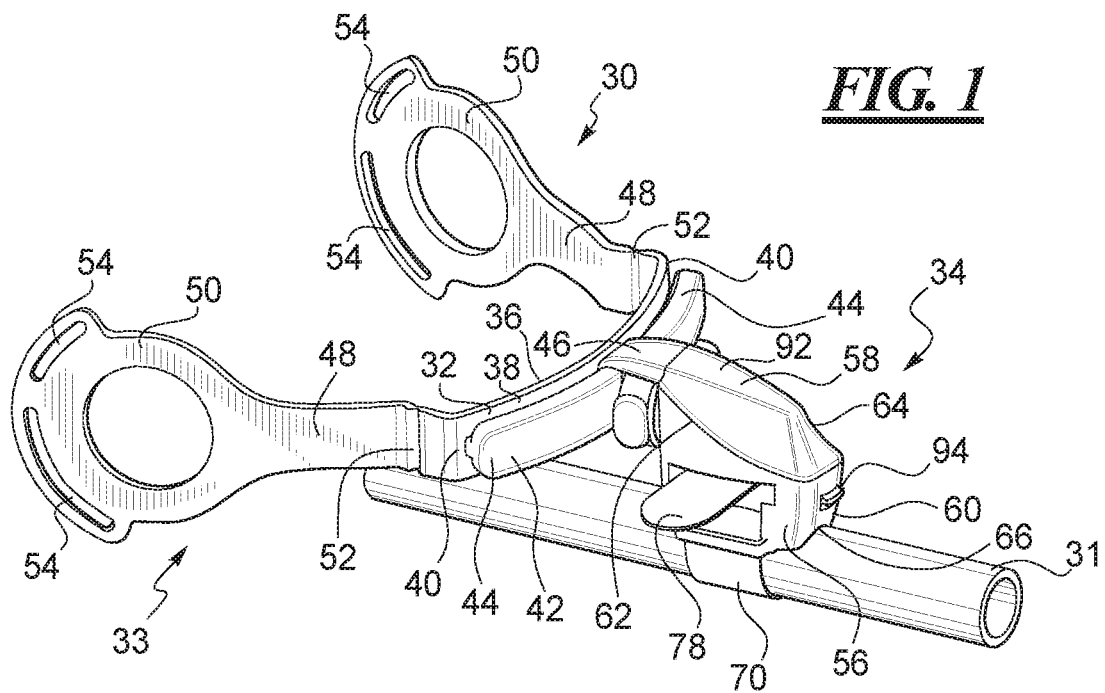
FIG. 1 is a perspective view of one embodiment of an ET tube holding device of the present disclosure.
Figure 2:
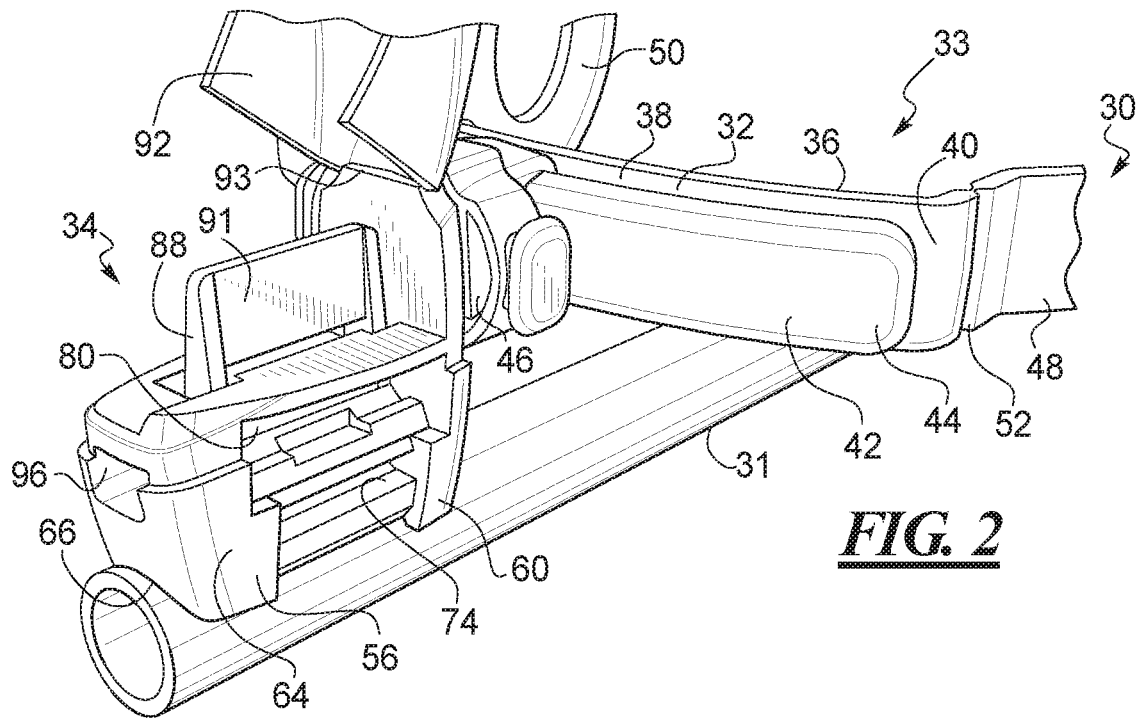
FIG. 2 is a partial perspective view of the ET tube holding device shown in FIG. 1.
Figure 8:
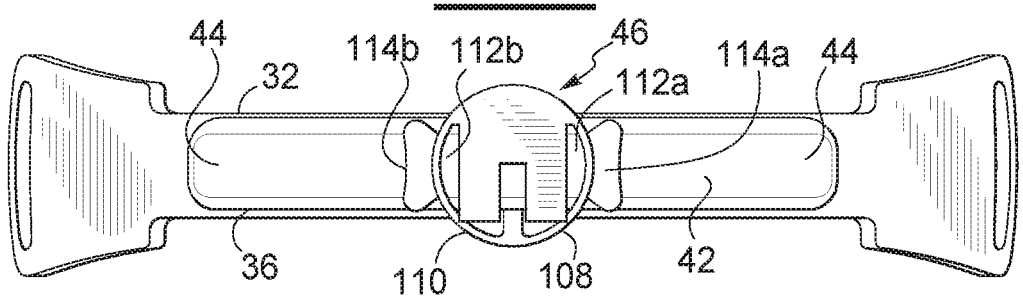
FIG. 8 is a front perspective view of the ET tube holding device of FIG. 1 with the tube holder removed and showing the features of the positioning member.
Figure 9:
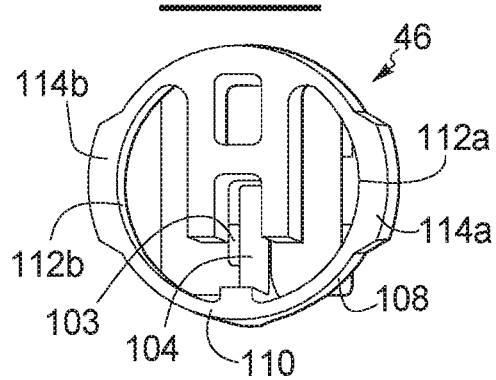
FIG. 9 is a back perspective view of the positioning member shown in FIG. 8.
Figure 10:
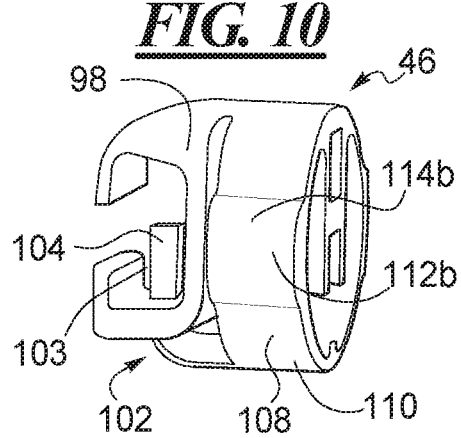
FIG. 10 is a side perspective view of the positioning member shown in FIG. 8.
Figure 11:
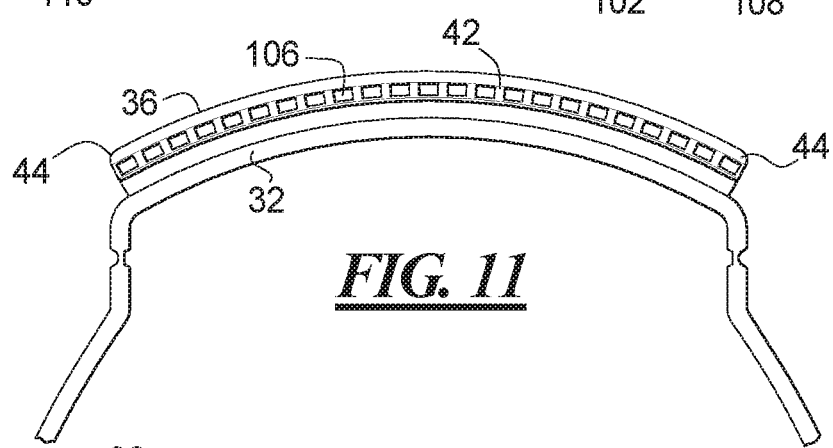
FIG. 11 is a bottom plan view of the ET tube holding device of FIG. 8 shown with the positioning member removed.

Turning now to the drawings, FIGS. 1-7 show one example of a device 30 for holding and securing a tube 31, such as an ET tube, on a patient. As shown in FIG. 1, the device 30 is an ET tube attachment device for securing an ET tube 31 to a patient, such as a patient requiring critical medical care. Device 30 generally includes a frame 33 that has an elongated central support or elongated central beam 32 that is configured to fit a lip on a patient's face and support a tube holder 34. In this particular example, the beam 32 is configured to rest above the patient's upper lip. However, the beam 32 can also be configured to rest below a patient's lower lip in another example. In each example, however, the beam 32 is intended to extend laterally or lie horizontally across a portion of the patient's face and support or carry the tube holder 34. Although the beam 32 can be positioned along either of the patient's lips, it may be preferable to position the beam along the patient's upper lip to avoid having movement of the patient's jaw affect positioning and performance of the device 30, and particularly the ET tube 31. The beam 32 has an inner side 36 that faces a patient's face and an exposed side 38 opposite the inner side 36. The beam 32 also has a pair of opposite ends 40.

The beam 32 may also have a rail 42 to which a tube holder 34 may be coupled or mounted. In the illustrated embodiment, the tube holder 34 is slidably mounted to rail 42 so as to be slidable along the rail 42 and preferably slidable along the rail 42 between the opposite ends 44 thereof. In other embodiments, the tube holder 34 may be non-slidably attached to beam 32. When the tube holder 34 is slidably mounted on rail 42, the device 30 may further include a positioning member 46 that allows selective lateral repositioning of the tube holder 34, as well as the ET tube 31 that is held or secured thereby, along the rail 42. The positioning member 46 may be releasably locked into position relative to rail 42 to allow selectively repositioning thereof. The positioning member 46 is configured to retain the tube holder 34 at a selected position along the rail 42 until the positioning member 46 is unlocked to allow movement thereof along the rail 42.

The beam 32 and/or rail 42 may be made of a tough, durable, semi-rigid, flexible, or very flexible material, such as polyethylene or polyurethane, and may be preformed or molded with a curved or arcuate shape to fit on a region of the patient's face adjacent to and along one lip of the patient. The beam 32 may have a length of between about 30 mm and about 60 mm. In one embodiment, the beam 32 may be designed to fit the smaller face of a pediatric or petite patient and may have a length of between about 30 mm and about 55 mm. For adult patients, the beam may have a length between about 50 mm and about 60 mm.

Extending from each end 40 of beam 32 is an arm 48 that has a cheek plate 50 at or adjacent to free end thereof. Between each arm 48 and the end 40 of the beam 32 is a hinge 52, such as the living hinge shown. The hinges 52 allow the frame 33 to accommodate difference sized faces and swelling of the patient's face, when such swelling occurs. The hinges 52 also allow the arms 48 to be folded inward so as to place the frame 33 in a compact configuration for storage and distribution.

A skin friendly cheek pad (not shown) may also be coupled to each of the cheek plates 50 on the inside face of each plate. The cheek pad can be an adhesive or an adhesive layer can be provided on the face contacting side of each of the cheek pads. The adhesive can be skin friendly and can help adhere the cheek plates 50 and beam 32 to the patient's face during use. Preferably, the cheek pads cover the cheek plates such that the cheek plates are prevented from contacting the patient's skin. The cheek pads may cover substantially the entire cheek plate. The cheek pads may cover the cheek plates and extend past the back end of the cheek plates, which in this embodiment would include extending past or covering the strap loops 54 (which are described in more detail below). In one embodiment, the outer edges of the adhesive layer, optionally, can be tapered in that the outer edges of the adhesive layer are thinner than toward the center of the layer. The tapering could be graduated in that the thickness of the adhesive layer gradually becomes thinner toward the outer edges. In other embodiments the thickness could change step-wise. Such tapering allows the adhesive to be more flexible at the edges and may aid in allowing the adhesive to better conform to the patient's face and could aid in the ease of attaching the straps to strap loops 54. The cheek plates 50 and pads may be curved or contoured to closely follow the curved contour of a patient's face. In the illustrated embodiment, the cheek plates 50 have a generally arcuate shape, which may be a circle, oval or ellipse. Furthermore, the check plates and/or check pads could include a writable surface. For example, the check plates and/or check pads could include a sticker or decal applied thereto wherein the sticker/decal includes a writable surface. In one embodiment, the medical personnel may write information pertaining to the patient on the writeable surface such as the date and time in which the device was applied to the patient.

Also, each cheek plate 50 in this example can have one or more strap loops 54 at or near their free ends. An adjustable head/neck strap, such as any of those disclosed herein or any other suitable head/neck strap, can be coupled to the frame 33 of device 30 via the strap loops 54 for securing the device 30 to a patient's head and aid in retaining the frame 33 on the patient's face. A separate lip pad (not shown) can be provided on the inner side 36 of the beam 32 as well. The beam 32 and/or lip pad may be any of those disclosed herein or any other suitable beam 32 and/or lip pad. The lip pad can be attached to the inner side 36 of the beam 32 and, optionally, can also have a skin friendly adhesive on the face side to help retain the frame 33 in position against the patient's face during use.

As will be evident to those having ordinary skill in the art, the beam, cheek plates, cheek pads, and head strap can vary in configuration and construction and yet fall within the scope of the invention and claims. The beam and cheek plates can be molded as one integrated plastic structure, if desired. The head strap can be formed having any suitable adjustable fastening mechanism, such as a hook and loop structure on a fabric strap. The cheek plates can be formed to have any number of configurations and constructions and can utilize a minimum amount of base material (i.e., plastic) and yet function as intended.

The tube holder 34 is attached to the positioning member 46, which is slidably mounted on the beam 32. The tube holder 34 includes a body or housing 56 having a top 58, bottom 60 and opposing sides 62, 64. The bottom 60 of the body 56 includes a surface 66 adapted to contact and/or receive an ET tube 31. In the illustrated embodiment the bottom surface 66 has a generally arcuate shape, such as a semi-circular or quarter-circular shape that is configured to receive the ET tube 31. As shown in FIGS. 2-7, the arcuate shaped surface may provide good contact for tubes of different sizes, tubes 31 and 31a. (It should be noted that the tubes 31 and 31a of these figures illustrate tubes of different sizes and do not illustrate co-extending tubes). In one embodiment, the arcuate bottom surface 66 may have a radius of between 2.0 mm and 7.0 mm. In another embodiment, the arcuate bottom surface may have multiple radii that may accommodate difference ranges of tube sizes. For example, as shown in FIG. 4A, the surface may include one radius to accommodate a larger tube 31 and a smaller radius to accommodate a smaller tube 31a. In the illustrated embodiment, the smaller radius portion is interspersed between the larger radius portions. In another embodiment, the radius may be between 2 mm and 6 mm which may be suitable for smaller or pediatric tubes such as tubes having an outer diameter (OD) of between 4 mm and 12 mm. For example, the arcuate surface may be sized to accommodate tube sizes between the sizes of 3 mm-8 mm, as they are commonly referred to in the field. In other embodiments, the arcuate surface may have a radius of between 4 mm and 7 mm which may be suitable to receive tubes having an OD of between 8 mm and 14 mm. For example, the arcuate surface may be sized to accommodate tube sizes between the sizes of 6 mm-10 mm, as they are commonly referred to in the field. The bottom surface 66, optionally, may be textured, which assists in reducing slippage of the ET tube. For example, the surface may also include ridges or tangs 68 (FIGS. 5 and 6), such as spikes, protrusions, nubs, etc. that contact the tube and frictionally and/or physically engage the ET tube to reduce slippage. In other embodiments, the bottom surface 66 of the body 56 may have other shapes or contours. For example, the bottom surface 66 may be flat.

A securement element, such as an elongated, flexible tube strap 70 for securing the ET tube 31 to the holder 34 is provided. One end of the tube strap 70 has an enlarged retaining portion 72 (FIG. 6). As shown in FIGS. 2-7, the body 56 includes a lower slot 74 extending therethrough for receiving the tube strap 70. The slot 74 has chamfered or recessed entries 76 (FIG. 5) on one side thereof so that the tube strap 70 can be threaded through the slot 74 and the retaining portion 72 can seat in the chamfered entries 76, fixing that end of the strap to the body 56. A free length 78 of the tube strap 70 can be wrapped around the ET tube 31 as shown in FIGS. 1 and 6. An adhesive pad (not shown) or layer, such as a suitable pressure-sensitive adhesive, optionally can be provided on an inner surface of the tube strap 70 to further restrain the ET tube 31 from rotational or longitudinal movement when secured against the bottom 66 of the body 56. The inner surface of tube strap 70 may also be a textured surface (i.e., include nub, spikes, tangs). When the bottom surface 66 of body 56 and/or the inner surface of the strap 70 are textured, the textured surfaces can impinge on the exterior surface of the ET tube 31 to frictionally and/or physically engaging the ET tube and further restraining the tube from movement. For example, the tube strap 70 and any other of the tube straps disclosed herein may include projections that impinge on the ET tube to assist in securing the tube. The projections may be made from plastic or metal. In one embodiment the projections may be mad from a MRI compatible metal.

An upper slot 80 extends through the body 56 and, after the free length 78 of the tube strap 70 has been wrapped around the ET tube 31, it is fed through the upper slot 80. The free length 78 may then be feed through slot 81 in the side of the housing to secure the free length 78 so that it is not undesirably in the way when the medical profession is moving the positioning member. The upper slot 80 includes a clamping member 82 that engages and clamps the free length 78 of the tube to secure it into place within slot 80. In the illustrated embodiment, the clamping member 82 is a cinch clamp that includes one or more pawls 84 (FIGS. 4, 5 and 7) that engage catches 86 (FIG. 6), such as ribs, recesses or teeth, on the free length 78 of the tube strap 70. Referring to FIG. 7, in one embodiment, the pawls 84 may be moved from an engaged position wherein the pawls 84 are engaged with the catches 86 on the free length 78 of the tube strap 70 and a disengaged position wherein the pawls 84 are disengaged from the catches 86 so that the strap 70 may be loosened or repositioned. For example, the pawls 84 may be attached to lever 88, which when moved, angles or positions the pawls 84 so that they are disengaged from the catches 86 on the free length 78 of the strap 70. In the illustrated embodiment, lever 88 extends through a vertical passage 90 (FIG. 7) within body 56 so that the top portion 91 of the lever 88 may be accessed and manipulated by the medical professional. The lever 88 may extend from the top of the body 56, or it may be covered by a reclosable lid 92 which prevents the patient from tampering with the lever 88 and/or prevents inadvertent movement of the lever 88. The reclosable lid 92 may be attached to the body 56 by a hinge 93 (FIG. 2) and may include a latch 94 (FIG. 3) on the end of the lid 92 opposite end the hinge 93 wherein the latch 94 engages a recess 96 (FIG. 2) of the body 56 to secure the closure of the lid 92 until is reopened. Additionally, as shown in FIGS. 5 and 6, the lid 92 may be configured to retain the lever 88 and pawls 84 in the clamped position. For example, the lid 92 may have a tapered slot 97 that receives the lever 88 and holds it and/or moves it into the engaged/clamped position when the lid 92 is closed.

Figures 12, 13, 14:
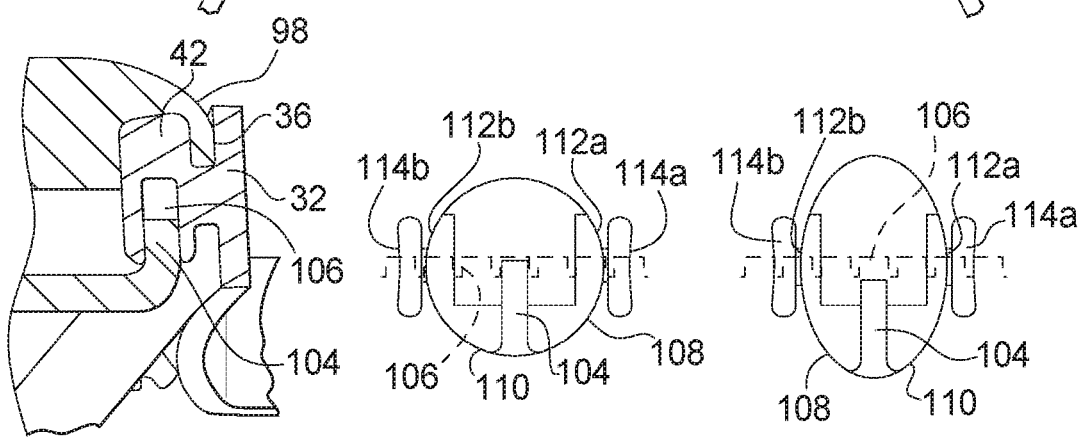
FIG. 12 is a partial cross-sectional view of the ET tube holding device, showing features of the positioning member and the rail.
FIG. 13 is a schematic illustration of the positioning member of FIG. 8 shown in an uncompressed and releasably locked position.
FIG. 14 is a schematic illustration of the positioning member of FIG. 8 shown in a compressed and unlocked position.

Referring to FIGS. 8-14, the positioning member 46 allows selective lateral positioning of the tube holder 34 and the ET tube 31 along the beam 32 without having to remove the device 30 from the patient or the ET tube 31 from the device. In this example, the rail 42 disposed on the exposed side 36 of the beam 32 and may have a smooth exposed surface. In one embodiment, the smooth exposed surface may include a design, decal or sticker. The design may be printed directly on the surface or may be on a sticker or decal applied to the surface, with for example an adhesive. Additionally, the surface could be a writeable surface, or the decal or sticker could include a writable surface. In one embodiment, the writable surface could be one in which the medical personnel could write information pertaining to the patient such as the date and time in which the device was applied to the patient. In pediatric applications, the design or sticker may be pleasing or calming to children. Referring to FIG. 12, the rail 42 may be generally T-shaped in cross-section (i.e., when viewed from the side of the device 30). The rail 42 is complementary shaped relative to a back side of the positioning member 46. For example, the illustrated positioning member 46 has a C-shaped sliding retainer 98 (FIGS. 10 and 12) that slides along, captures, and engages the rail 42. The T-shaped rail 42 and C-shaped retainer 98 can fit snuggly to one another but without impeding lateral sliding movement of the positioning member 46 along the rail 42. One or more stops (not shown) may be provided at each of the opposite ends 44 of the rail 42 to keep the positioning member 46 from sliding off either end 44 of the rail 42 during use. These stops can allow the positioning member 46 to be snapped onto one end of the rail 42 during assembly of the device 30.

The positioning member 46 also includes a locking member 102 that engages the rail 42 to positively lock and hold the tube holder 34 and ET tube 31 in the selected position of adjustment on the rail 42. In the illustrated embodiment, as shown in FIGS. 9, 10 and 12-14, the locking member 102 includes at least one post or prong 104 that engages catches 106, such as recesses or ribs, spaced apart along the bottom side and/or top side of the rail 42. In the illustrated embodiment, the post 104 extends through an opening 103 in the bottom of the C-shaped retaining member 98 to engage the catches 106 in the bottom of the rail 42. The positioning member 46 includes an actuator that may be actuated to move the post 104 into and out of engagement with the catches 106. In the illustrated embodiment, the actuator is a biasing member 108 that biases the post 104 into engagement with the catches 106 and can be actuated to disengage the post 104 from the catches 106 (FIGS. 13 and 14). The biasing member 108 has a generally arcuate shape, such as a circular shape, elliptical shape or oval shaped. In one embodiment the biasing member 108 may be at least a quarter circle, at least a semi-circle or substantially a full circle. In the illustrated embodiment, the post 104 is connected to the bottom 110 of the arcuate biasing member 108. The post 104 has a generally L-Shape wherein one leg of the L-shape is connected to the bottom 110 of the arcuate member and the other end of the L-shape is configured to engage catches 106 on the bottom of the rail 42. When the sides 112a and 112b of the arcuate member 108 are pinched or compressed inward, the bottom 110 of the biasing member 108 moves outward or away from the center of circle or of the arc. In this compressed position, the post 104 is disengaged from the catches 106 at the bottom of the rail 42 (FIG. 14). Optionally, the sides 112a and 112b of the arcuate biasing member 108 may include finger gripping members 114a and 114b that can be gripped and compressed/pinched inward by the medical professional. When the post 104 is disengaged from the catches 106, the tube holder 34 and positioning member 46 can slide along the rail 42 to a desired position along the rail. This can be done to allow medical personnel to access the patient's mouth without having to remove the device 30 or the ET tube 31. When pressure on the sides 112a and 112b of the arcuate biasing member 108 is released, the post 104 will return and engage the catches 106 to retain the tube holder 34 in the selected position along the rail 42 (FIGS. 12 and 13).

FIGS. 15-17 illustrate another embodiment of a tube holder 116 of the present disclosure. Tube holder 116 may be used with the frames and positioning mechanism as described herein or may be use with any other suitable tube holder device. In this embodiment, the tube holder 116 includes a housing 118 and a carriage 120 wherein the ET tube 31 is securely held or clamped between the carriage 120 and the bottom 122 of the housing 118. In the illustrated embodiment, the carriage 120 moves away from the bottom 122 of the housing 118 to define a space for accepting an ET tube 31 and then moves toward the bottom 122 of the housing 118 to hold or clamp the tube 31 between the carriage 120 and the housing 118.

The housing 118 of the tube holder 116 has an opening 124 in the top end 126 and an opening 128 in the bottom end 122. In the illustrated embodiment, the top end 126 has a generally cylindrical shape and the bottom end 122 has a generally rectangle shape. In other embodiments, the top and bottom ends may be the same shape or have other shapes. Referring to FIG. 16, the housing includes an internal partition 130, which may be a horizontal wall, that partitions the top end 126 of the housing 118 from the bottom end 122 the housing 118. In other embodiments, the partition 130 may be a partial wall or a plurality of struts in a web-like arrangement.

The carriage 120 includes a lower portion 132 having a configuration for receiving an ET tube. For example, the lower portion 132 of the carriage 120 may have a generally C-Shaped configuration. The carriage 120 also includes a post 134 extending upward from the lower portion 132 of the carriage 120. As shown in FIG. 16, when an ET tube is not being held by the holder 116, the lower portion 132 of the carriage 120 may at least partially reside within the bottom opening 128 of the housing 118 with the post 134 extending through a hole 136 in the partition 130. The top end 138 of the post 134 is connected to an actuator 140 located in the top opening 124 of the housing.

In the illustrated embodiment, the actuator 140 has a shape that generally matches the shape of the top opening 124 of the housing 118. In the illustrated embodiment, the actuator 140 is a generally cylindrically shaped button. The actuator 140 has an open bottom end 142 and is generally hollow such that the post 134 of the carriage 120 extends though the actuator 140 and is connected to the undersurface of the top wall 144 of the actuator 140 by, for example, a friction or snap fit with a connecting element (not shown) on the undersurface of the top wall 144 of the actuator or by an adhesive.

The tube holder 116 also includes a biasing member 146 that biases the actuator 140 upward from the top end 126 of the housing 118, which results in moving the lower portion 132 of the carriage 120 toward the bottom end 122 of the housing 118. The biasing member 146 may be plastic, rubber, elastomeric, or metal and is preferably made of a material that is compatible with MRI use, e.g. made from plastic or an MRI compatible metal such as nonferromagnetic materials including but not limited to tantalum, commercially pure titanium, and nonferromagnetic forms of stainless steel. In the illustrated embodiment, the biasing member 146 is a helical spring, the top end 148 of which contacts the undersurface of the top wall 144 of the actuator 120 and the bottom end 150 of which contacts the partition 130. In this example, the post 134 of the carriage 120 extends through the center of the helical spring. Other embodiments could include different types of biasing members or a plurality of biasing members, including elastomeric bladders, coiled springs, sheet springs, plungers, or the like. The biasing member 146 biases the actuator 140 upward, which in turn pulls the carriage 120 upward toward the bottom 122 of the housing 118 and into the opening 128 in the bottom 122 of the housing 120, when an opening is present. In some alternative embodiments, the bottom 122 of housing 120 may be a substantially continuous surface and may not include an opening for receiving the lower portion 132 of carriage 120.

To secure an ET tube to the holder 116, a medical professional pushes the actuator 140 downward into the top opening 124 of the housing 118 which in turn moves the carriage 120 downward relative to the bottom 122 of the housing 118 to define a space for accepting the ET tube 31 therebetween. Once the ET tube 31 is positioned in the desired position, the medical professional releases the actuator 140 which is biased by the biasing member 146 back toward the upward position. As the actuator 140 moves upward it pulls the carriage 120 with it, thereby clamping the ET tube 31 between the lower portion 132 of the carriage 120 and the bottom end 122 of the housing 118. In the illustrated embodiment, the bottom end 122 of the housing 118 may have generally arcuate or arced surfaces or recesses 150 configured to accept an ET tube. In one embodiment, the arcuate surface(s) 150 may have a radius of between 2.0 mm and 7.0 mm. In another embodiment, the arcuate bottom surface may have multiple radii that may accommodate difference ranges of tube sizes, such as that described above with respect to FIG. 4A. In another embodiment, the radius may be between 2 mm and 6 mm which may be suitable for smaller or pediatric tubes such as tubes having an outer diameter (OD) of between 4 mm and 12 mm. For example, the arcuate surface may be sized to accommodate tube sizes between the sizes of 3-8, as they are commonly referred to in the field. In other embodiments, the arcuate surface may have a radius of between 4 mm and 7 mm which may be suitable to receive tubes having an OD of between 8 mm and 14 mm. For example, the arcuate surface may be sized to accommodate tube sizes between the sizes of 6-10, as they are commonly referred to in the field.

The bottom surface 150 of the housing 118 and the lower portion 132 of the carriage 120, optionally, may be textured, which assists in reducing slippage of the ET tube. For example, the surface may also include ridges or tangs 151, such as spikes, protrusions, nubs, etc. that contact the tube and frictionally and/or physically engage the ET tube to reduce slippage.

Figure 18:
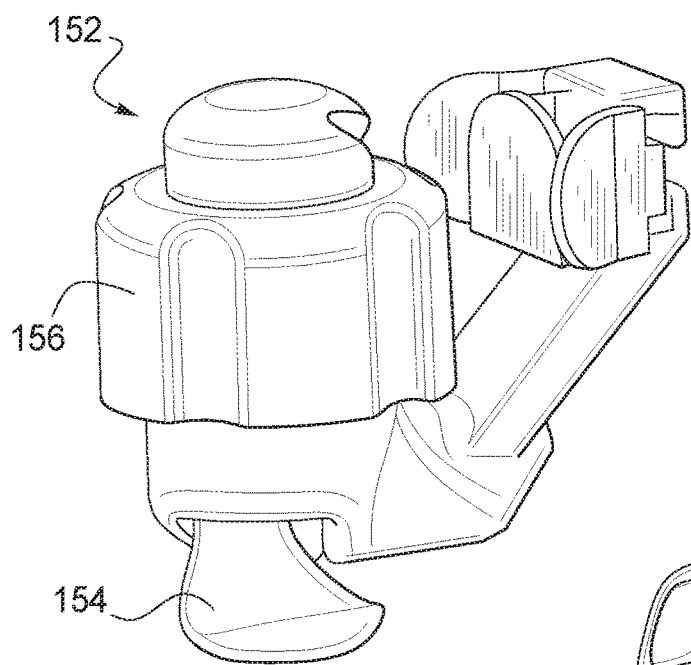
FIGS. 18 and 19 are perspective views of another embodiment of a tube holder in accordance with the present disclosure.
Figure 19:
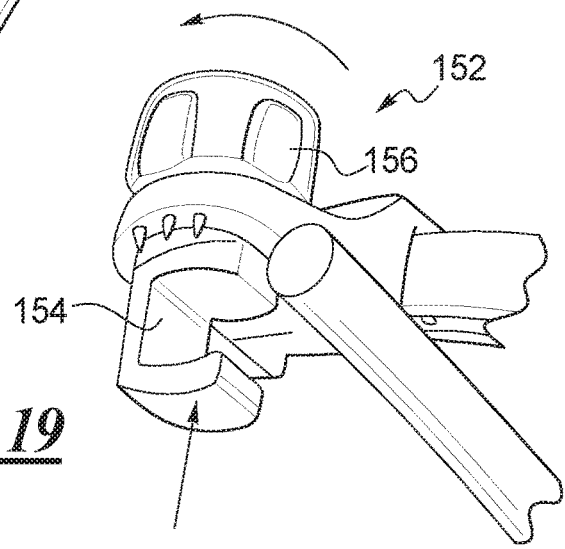
Figure 20:
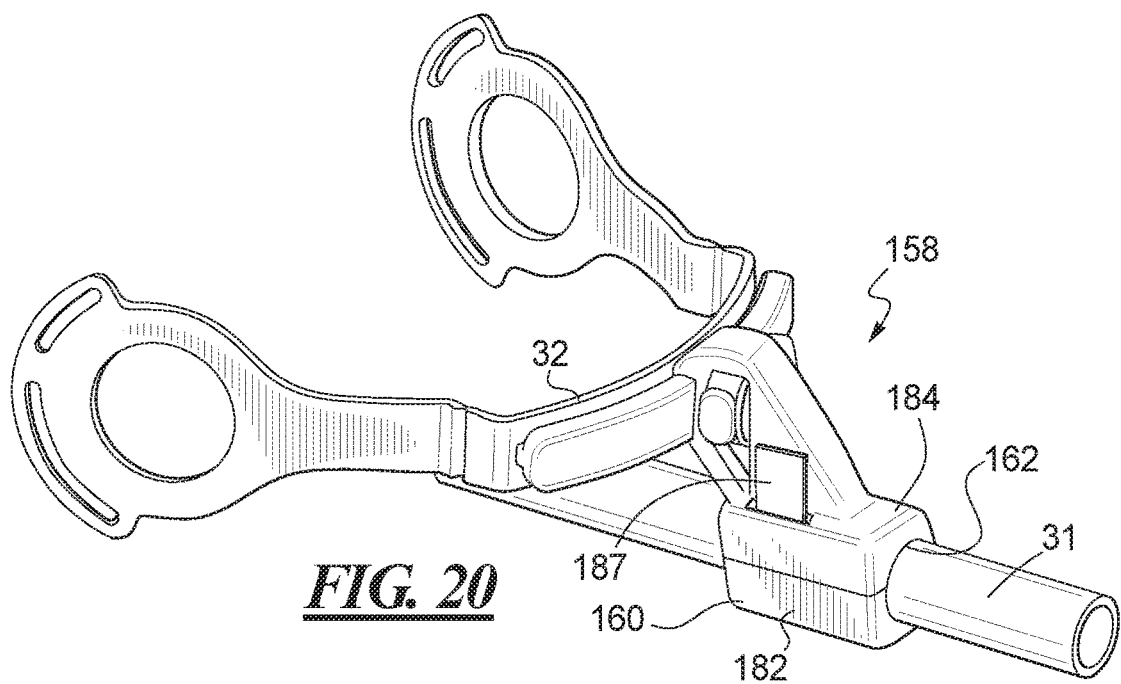
FIG. 20 is a perspective view of another embodiment of a tube holder in accordance with the present disclosure.

FIGS. 18 and 19 illustrate another embodiment of a tube holder 152 wherein movement of the carriage 154 is actuated by rotatable actuator 156.

Figure 21:
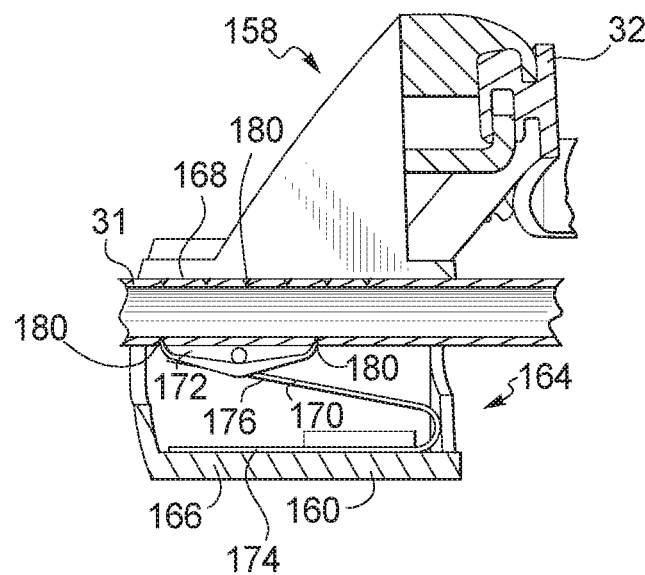
FIG. 21 is a cross-sectional view of the tube holder of FIG. 20.
Figure 22:
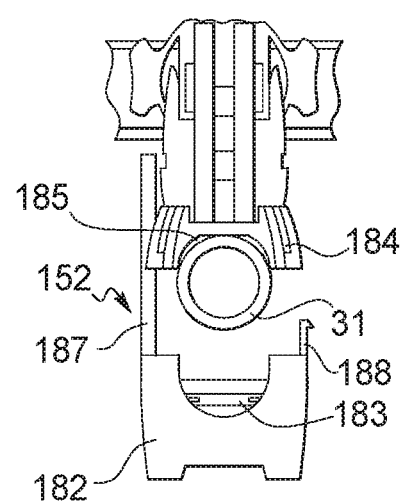
FIG. 22 is a front elevation view of the tube holder of FIG. 20.
Figure 23:
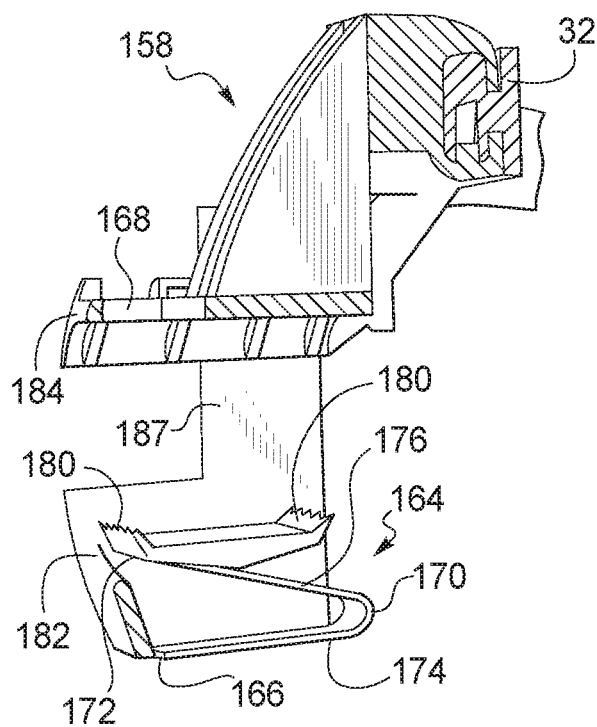
FIG. 23 is a partial cross-sectional view of the tube holder of FIG. 20.
Figure 24:
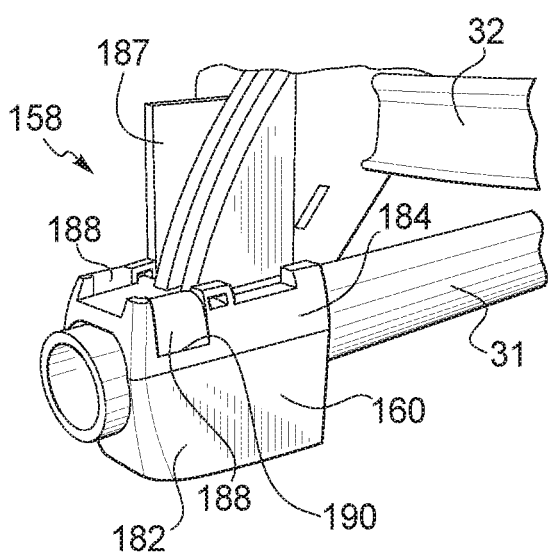
FIG. 24 is a perspective view of the tube holder of FIG. 20.

FIGS. 20-24 illustrate another embodiment of a tube holder 158 of the present disclosure. Tube Holder 158 may be used with a frame and/or positioning mechanism as described above or may be use with any other suitable tube holder device design. In this embodiment, the tube holder 158 includes a housing 160 having a passageway 162 therethrough for receiving and holding an ET tube 31. (Similar to above the larger and smaller tubes are to illustrate that the device may accommodate tubes of different sizes and these tubes do not illustrate two or dual lumen tubes). The passageway 162 may be generally arcuate and extends generally perpendicular to the beam 32 of the holder device. As shown in FIGS. 21 and 23, a clamping member 164 is located within the housing 160 for clamping the ET tube 31 against an internal surface of the housing 160. In the illustrated embodiment, the clamping member 164 is associated with bottom wall 166 of the housing 160 and clamps the ET tube 31 against the top wall 168 of the housing 160. In other embodiments, the clamping member 164 could be associated with the top wall 168 and clamp the ET tube against the bottom wall 166.

The clamping member 164 may include a biasing member 170 and clamping arm 172. The biasing member 170 may be plastic or metal and is preferably made of a material that is compatible with MRI use, e.g. made from plastic or an MRI compatible metal such as nonferromagnetic materials, including but not limited to tantalum, commercially pure titanium, and nonferromagnetic forms of stainless steel. In the illustrated embodiment, the biasing member 170 is generally V-Shaped spring. Other embodiments could include different types of biasing members or a plurality of biasing members, including but not limited to elastomeric bladders, coiled springs, sheet springs, plungers, or the like. The V-Shaped spring is turned on its side wherein the bottom leg 174 of the V-shaped spring is attached to and extends along the bottom wall 166 of the housing 160 and the top leg 176 of the spring extends at an angle upward. A clamping arm 172 is attached to the free end of the top leg 176. When an ET tube 31 is located within the passageway 162 defined by the housing 160, the force of the spring pushes up on the clamping arm 172 to clamp the ET tube 31 between the clamping arm 172 and the top wall 168 of the housing 160. The top wall 168 of the housing 160 and/or the clamping arm 172 of the clamping member 164, optionally, may be textured which assists in reducing slippage of the ET tube 31. For example, the surfaces may also include ridges or tangs 180, such as spikes, protrusions, nubs, etc. that contact the ET tube and frictionally and/or physically engage the tube to reduce slippage.

As shown in FIGS. 22 and 23, the housing 160 may be openable to allow positioning of the ET tube 31 into the passageway 162. For example, the housing 160 includes a bottom portion 182 that is separable from a top portion 184. The bottom portion 182 may include one or more arcuate surfaces 183 that from one part of the passageway 162 and top portion 184 may also include one more actuate surfaces 185 that form another part of the passageway 162 (FIG. 22). The bottom portion 182 includes or is attached to an upward projecting arm 187 wherein the arm 187 is slidably mounted to the top portion 184 of the housing 160. The arm 187 slides up and down relative to the top portion 184 of the housing 160 to move the bottom portion 182 of the housing toward and away from the top portion 184. To place an ET tube 31 into the passageway 162 of the housing 160, the bottom portion 182 is moved away from the top portion 184 and the tube 31 is placed in the space between the top and bottom portions 182, 184. For example, the tube 31 may be placed against the top portion 184 of the housing 160. The bottom portion 182 is then moved into contact with the top portion 184, thereby closing the housing 160. When the housing 160 is closed, the tube 31 is clamped between the clamping member 164 and the top wall 168 of the housing 160. The housing 160 may be maintained in a closed position by latches 188 which project upward from the bottom portion 182 of the housing and are received into openings 190 in the top portion 184 of the housing 160. The latches 188 may have shoulders (not shown) that engage a ridge (not shown) associated with openings 190 in the top portion 184 of the housing 160 to maintain the housing in a closed position. The latches 188 may be flexible so that when pinched inward, the shoulders disengage the ridges to allow the bottom portion 182 to again be moved away from the top portion 184 for opening of the housing 160.

Figure 25:
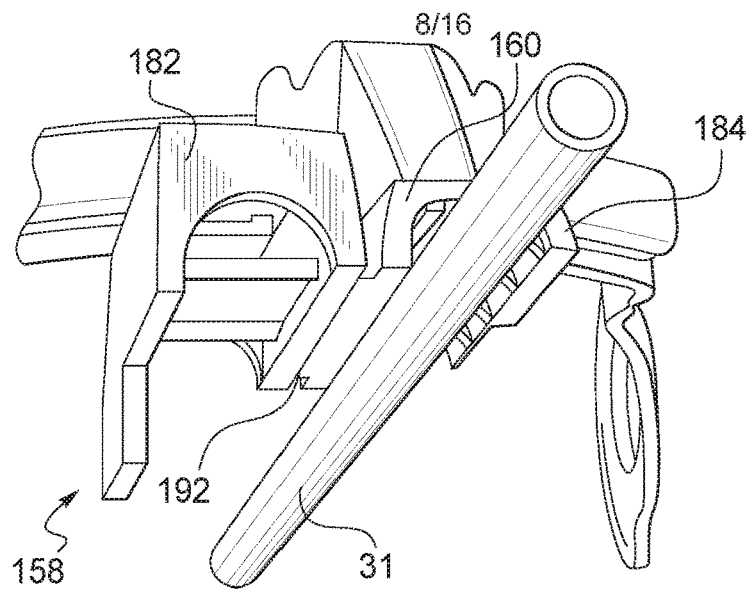
FIG. 25 is a perspective view of another embodiment of a tube holder of the present disclosure.
Figure 26:
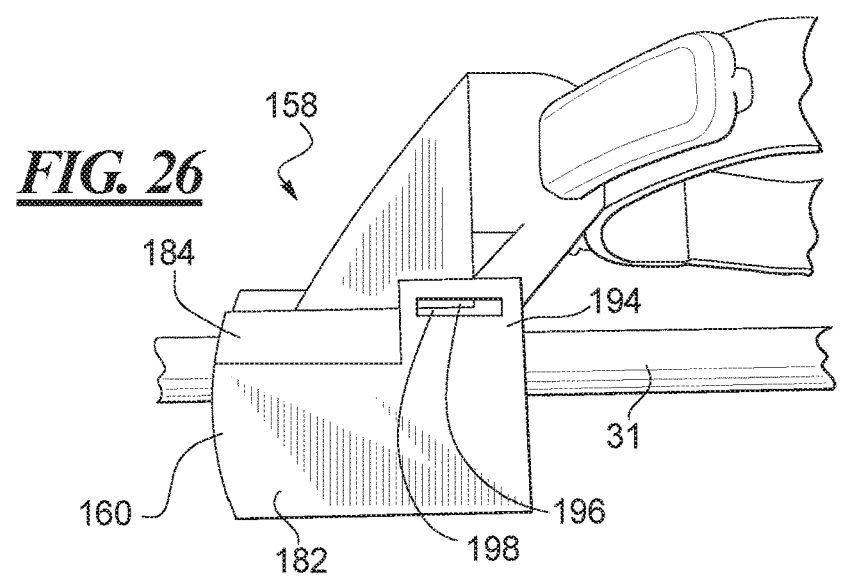
FIG. 26 is a side perspective view of tube holder of FIG. 25.

FIGS. 25 and 26 illustrate another embodiment of holder 158 wherein the bottom portion 182 of the housing 160 is connected to the top portion 184 by a hinge 192, which may be a living hinge or a piano/continuous hinge, for example. To place the ET tube 31 within the housing, the bottom portion 182 may be rotated to open the housing 160. The ET tube 31 may then be placed in the housing 160, e.g. against the upper portion of the passageway defined by the top portion 184 of the housing 160. After the tube 31 is in place, the bottom portion 182 may be rotated back into the closed position. The housing 160 may include a releasable locking mechanism to releasable lock the housing 160 in the closed position. In the illustrated embodiment, the bottom portion 182 includes an upstanding tab 194 which has an opening 196 therein. When the housing 160 is in the closed position, the opening 196 of the tab 194 receives a projection 198 extending from the top portion 184 of the housing 160 to releasably lock the housing in the closed position. To open the housing 160, the medical professional presses on the tab 194 to outwardly flex it and disengage the projection 198 from the opening 196 which allows the bottom portion to then again be rotated to the open position.

Figure 27:
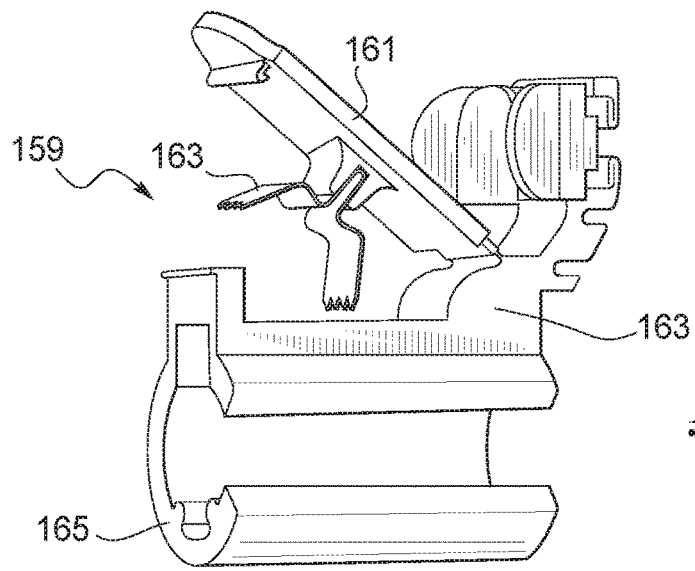
FIG. 27 is perspective view of another embodiment of a tube holder of the present disclosure.

FIG. 27 illustrates an embodiment of a tube holder 159 wherein the biasing member 163 is associated with a top wall 161 of the housing 163 and clamps a tube to the bottom wall 165 of housing 163.

The use of a tube holder having a biasing member that affects clamping or holding of the tube, such as those described about in FIGS. 15-17 and 20-27, may provide the advantage of having a uniform clamping force wherein the medical professional is not arbitrarily selecting the clamping force, which commonly occurs in devices that use tube straps. This is because, the biasing force of the biasing member may be tailored or tuned to provide a uniform clamping force. In one embodiment, the biasing member may be tailored to clamp small sized tubes that are used in pediatric settings, or the biasing member may be tailored to clamp larger tubes that are used for adult applications. In yet another embodiment, the biasing member may be tailored to clamp tubing sizing ranging from pediatric tubes to adult tubes.

FIG. 28 illustrates a prior art head/neck strap or band 200 that is attached to strap loops 202 and encircles a patient's head/neck to assist in securing the tube holder device 204 to the patient. The head/neck strap 200 is preferably made of a flexible, soft cloth. The head/neck strap 200, optionally, may have an enlarged segment 206 that comfortably fits against the back of a patient's head/neck and holds the strap 200 in place. Elongated strap segments 208 and 210 extend from enlarged segment 206 and can be threaded through respective strap loops 202, then reversed and attached to themselves by clamps (not shown) or, preferably, by using fabric loop and hook-type retainers commonly known and sold under the trademark "Velcro". Where Velcro is employed, flexible end straps 212 with hooks can be attached to the ends of strap segments 208 and 210 for attaching to the cloth of the band 200 which includes loops.

FIG. 29 illustrates one embodiment of a head strap 216 wherein one or both of the strap segments 218 include a length or segment of stretchable fabric 220, such as an elastic band.

FIG. 30 illustrates another embodiment of a head strap 222 that is of a two-piece construct. The first segment 224 may be a long piece of loop material one end 226 of which includes a tapered securing member 228 that includes hook material. This end 226 is configured to be inserted into a strap loop of a holder device and folded back on itself so that the hooks and loops engage to secure the strap to the holder device. The second segment 230 may be a shorter piece of loop material, one end 231 of which is attached to a securing member 232 that includes hook material. The hook material of securing member 232 engages the loop material of the first segment 224 at the other end 227 thereof to releasably secure the second segment 230 to the first segment 224. The second segment 230 also includes a securing member 234 at the other end 236 thereof wherein the securing member 234 includes hook material. End 236 of the second segment 230 is configured to be inserted into the other strap loop of a holder device and folded back onto itself or onto the first segment 224, wherein the hooks of the securing member 234 engage one or both of the loop material of the first segment 224 or second segment 230 to secure the strap to the holder device. This two piece configuration allows the strap 222 to be adjusted at the side of the patient's face as opposed to the back of the patient's neck. Also the end 227 of the first segment 224 may be cut to length to provide a custom fit to the patient.

The first and second segments 224 and 230 may have a variety of different lengths and sizes. For example, the first segment 224 and second segment 230 may be proportioned so that the ratio between the lengths of the first and second segments enables adjustment of the strap at the side of the patient's head. Additionally, each of the securement members may have different lengths. For example, the securement members 228, 232 and 234 may have a length of between about 2.5 inches and about 3.5 inches. The lengths of the first and second segments 224 and 230 may be varied depending on the application and in one embodiment may be sufficiently long to accommodate encircling a cervical collar.

FIG. 31 illustrates another embodiment of a head/neck strap 238 that has similar structure and features to that of band strap 222 of FIG. 30 except that the second segment 240 includes a length or segment 242 of elastic material.

Any of the head/neck straps disclosed herein may include a variety of designs, e.g., wording, symbols, or patterns printed/embossed on it. In a pediatric application it may be desirable to have designs pleasing or comforting to children, such as comforting images of teddy bears or rainbows or a camouflage design.

As shown in FIG. 32, the head/neck strap 244 may also include a disposable paperboard/plastic introducer 246 that can be pre-attached or attached to a loop end of strap. The introducer assists the medical professional in sliding the strap 244 and the patient's neck/head and then can be removed to allow attachment of the strap to the tube holder device. This reduces the need to lift the patient's head while installing the holder device to the patient.

Figure 33:
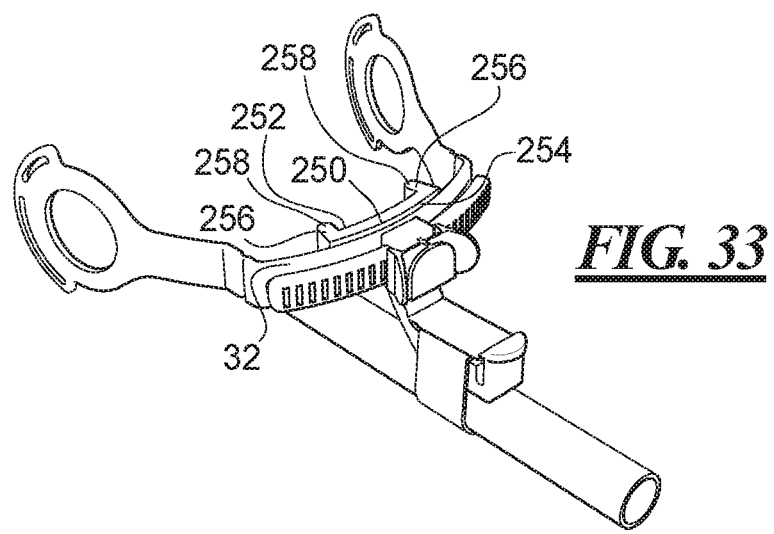
FIG. 33 is a perspective view of a tube holder device showing one embodiment of a lip pad of the present disclosure.
Figure 34:
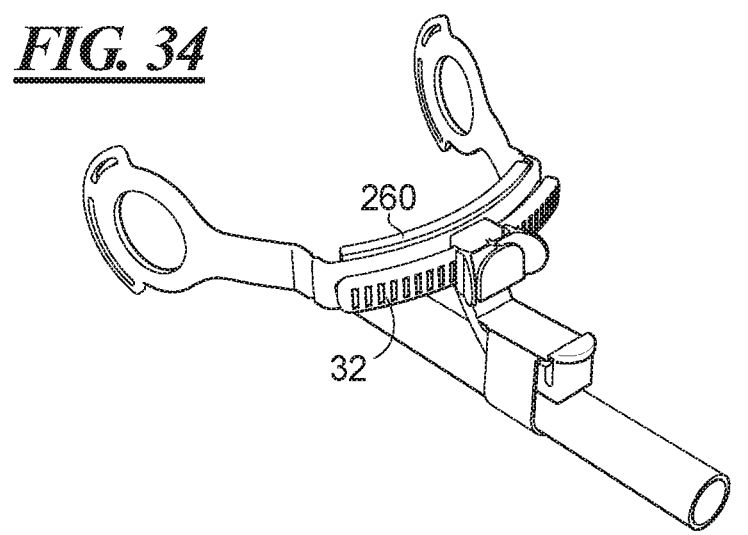
FIG. 34 is a perspective view of a tube holder device showing another embodiment of a lip pad of the present disclosure.

FIGS. 33 and 34 illustrate lip stabilizers or pads of the present disclosure. The lip pads may be used with any of the holder devices and tube holders disclosed herein or any other suitable ET tube holder devices. Additionally, the lip pads may be made from semi-rigid foam or memory foam, and the foam may be open celled foam or closed cell foam. In FIG. 33, the lip pad 250 may assist in alleviating pressure on the patient's maxillofacial region. The lip pad 250 is an elongated member having an inner side 252 configured to contact the patient's face above the patient's lip. The lip pad 250 also includes an outer beam attachment side 254 that is attached to the beam 32 by, for example, adhesive. Each of the ends 256 of the lip pad 250 is enlarged or includes a projecting portion 258 that projects toward and contacts the patient's face.

In FIG. 34, the lip pad 260 is an elongated member that has substantially the same length or extends substantially along the full length of the beam 32. The lip pad 260 being substantially the same length as the beam spreads out the pressure over a greater surface area, which may assist in alleviating the concentration of pressure on the patients face.

Figure 35:
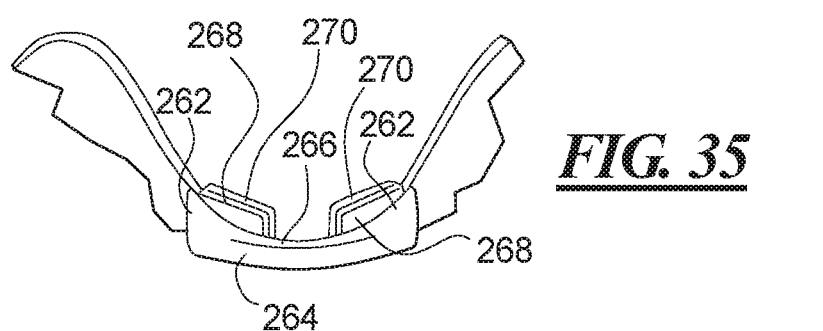
FIG. 35 is a perspective view of one embodiment of a frame of a tube holder device of the present disclosure.
Figure 36:
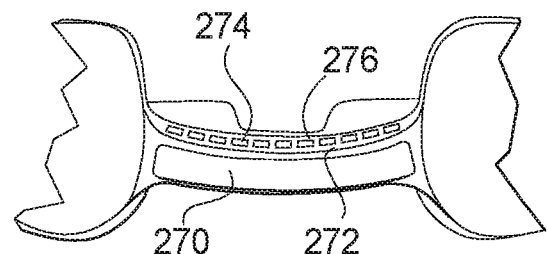
FIG. 36 is a perspective view of another embodiment of a frame of a tube holder device of the present disclosure.

FIGS. 35 and 36 illustrate beams that may be used with any of the holder devices and tube holders disclosed herein or any other suitable ET tube holder devices. In FIG. 35, each end 262 of the beam 264 on the inner or face side 266 thereof includes a tab 268 that projects inward toward the center line of the face. Optionally, the tabs 268 may include lip pads 270. When the device is placed on the patient's face, the tabs 268 contact the area of the patient's face above the lips. The tabs 268 have sufficient flexibility so that they flex to alleviate or accommodate pressure. For example, if the patient's face swells, the tabs 268 will deflect to accommodate such swelling.

In FIG. 36, the beam 270 includes an outer strut 272 and an inner strut 274 which are attached to each other at the ends thereof and define a space 276 therebetween. The outer and inner struts 270 and 272 have sufficient flexibility so that the beam 270 flexes to accommodate force, such as when force is generated on the beam 270 from the swelling of a patient's face.

FIGS. 37 and 38 illustrate another device 330 for holding and securing a tube (not shown) on a patient. Device 330 may include a frame 333 and positioning member 346 having the same or similar features as the above-discussed frames and positioning members. The frame and/or positioning member, alternatively, may be any other suitable frame or positioning member. In the illustrate embodiment, the frame 330 has an elongated central support or elongated central beam 332 that is configured to fit adjacent to a lip on a patient's face and support a tube holder 334. The beam 332 may also have a rail 342 to which the tube holder 334 may be coupled or mounted, as described earlier with respect to FIGS. 8-13. When the tube holder 334 is slidably mounted on rail 342, the device 330 may further include a positioning member 346 that allows selective lateral repositioning of the tube holder 334 along the rail 342, as also described earlier.

The tube holder 334 includes a housing 336 having a passageway 338 therethrough for receiving and holding an ET tube. The passageway 338 may be generally arcuate and extends generally perpendicular to the beam 332 of the frame 333. A tube clamping member 340, which may be the same as or similar to the clamping member shown in FIGS. 21 and 23 and described above, is located within the housing 336 for clamping the ET tube against an internal surface of the housing 336.

Figure 42:
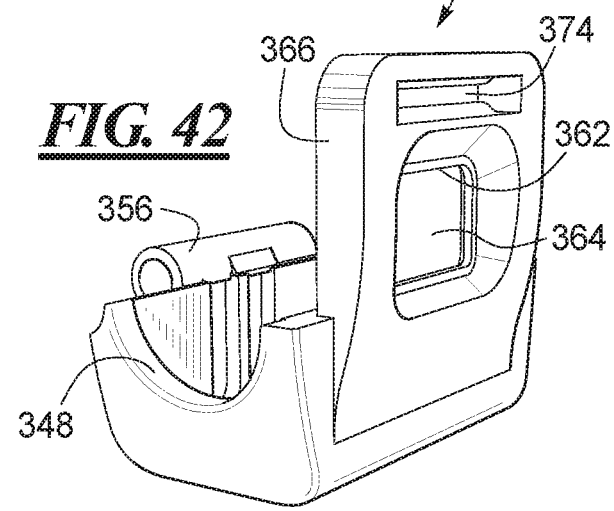
FIG. 42 is a perspective view of the bottom housing of the tube holder of FIG. 37.

The housing 336 may be moved to an opened position to allow for positioning of the ET tube into the passageway 338. The housing 336 may then be moved to a closed position for holding the tube within the passageway 338. In the illustrated embodiment, the housing 336 includes a bottom portion 344 that is separable from a top portion 346. Referring to FIGS. 37, 38 and 42, the bottom portion 344 may include one or more arcuate surfaces 348 that define at least a part of the passageway 338. Similarly, referring to FIG. 38 the top portion 346 may include one or more arcuate surfaces 350 that define at least a part of the passageway 338. Furthermore, the bottom surface 351 of the top portion 346 of the housing 336 may be textured for holding and gripping a tube. For example, in FIG. 40, the bottom surface 351 may include spikes 353.

Figure 40:
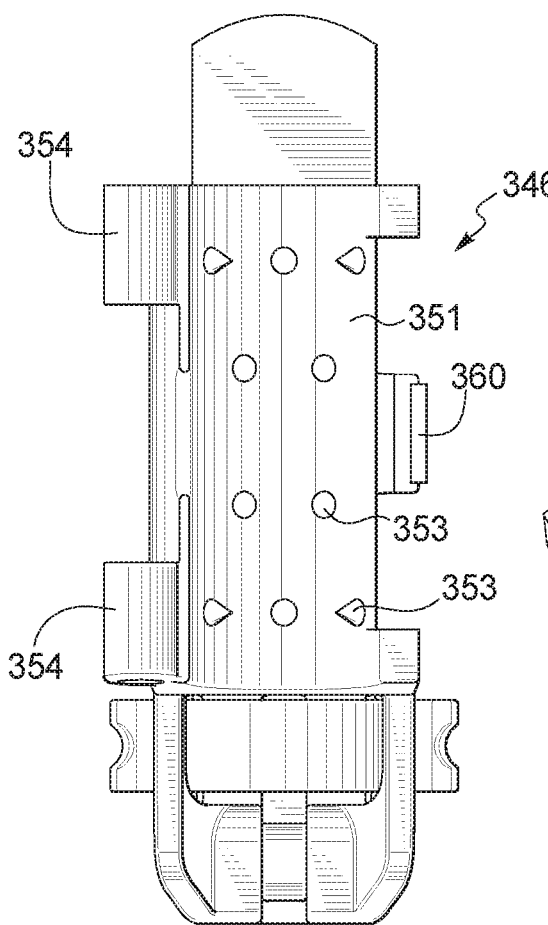
FIG. 40 is a bottom view of the top housing of the tube holder of FIG. 37.

In one embodiment, the bottom portion 344 may be hingedly connected to the top portion 346, by for example, a piano hinge 352 (FIG. 38) located on one side of the housing 336. In the illustrated embodiment, hinge 352 includes knuckles 354 on the top portion 346, as shown in FIGS. 38 and 40, and knuckle 356 on the bottom portion 344. Knuckles 354 and 356 are held together by a pin.

Referring to FIGS. 37, 39, 41 and 42, on the side of the housing 336 opposite the piano hinge 352, there may be a releasable locking member 358 (FIG. 37) for releasably locking the top and bottom portions 344 and 346 of the housing 336 in the closed portion. The releasable locking member 358 includes a post or shoulder located on one of the top portion and bottom portion. The locking member 358 also includes an edge that that defines an opening on the other of the portions, wherein the post enters the opening and engages the shoulder to lock the portions in the closed position.

Figure 41:
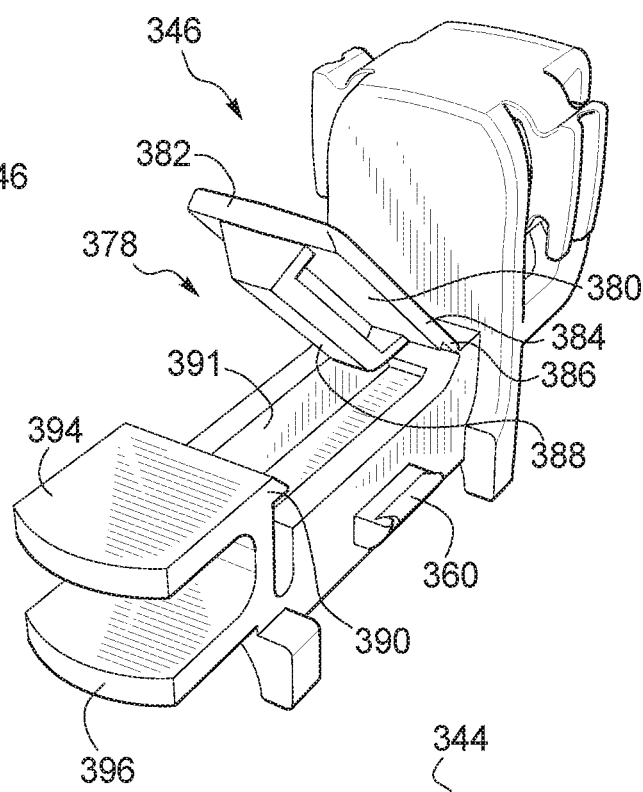
FIG. 41 is a top perspective view of the top housing of the tube holder of FIG. 37.

Referring to FIGS. 39-41, in the illustrated embodiment, the shoulder 360 is located on a side of the top portion 346. Turning to FIG. 42, the edge 362 defining the opening 364, which accepts shoulder 346, is located on the bottom portion 344. The edge 362 defining the opening 364 is located in an upstanding wall 366 of the bottom portion 344. To lock the top and bottom portions 344 and 346 in the closed position, the bottom portion 344 is moved about hinge 352 to bring the bottom and top portions 344 and 346 together and into the closed position. In the closed position, the upstanding wall 366 of the bottom portion 344 passes by the side wall of the top portion 346. The shoulder 360 extending from the side of the top portion 346 enters the opening 364 in the upstanding wall 366 and engages the edge 362 to lock the housing 336 in the closed position. To unlock the housing 336, the medical professional pushes outward on the upstanding wall 366 to disengage the edge 362 from the shoulder 360. The bottom portion 344 can then be rotated about the hinge 352 to the opened position.

Figure 43:
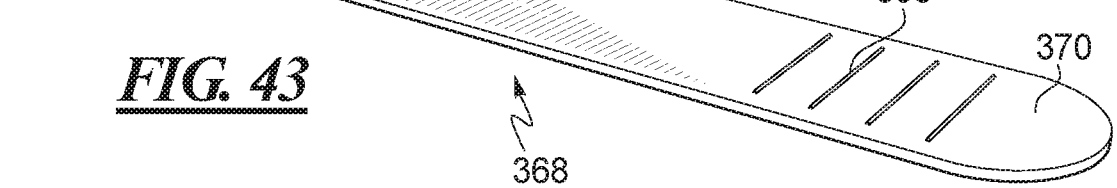
FIG. 43 is a perspective view of the retaining member of FIG. 37.
Figure 48:
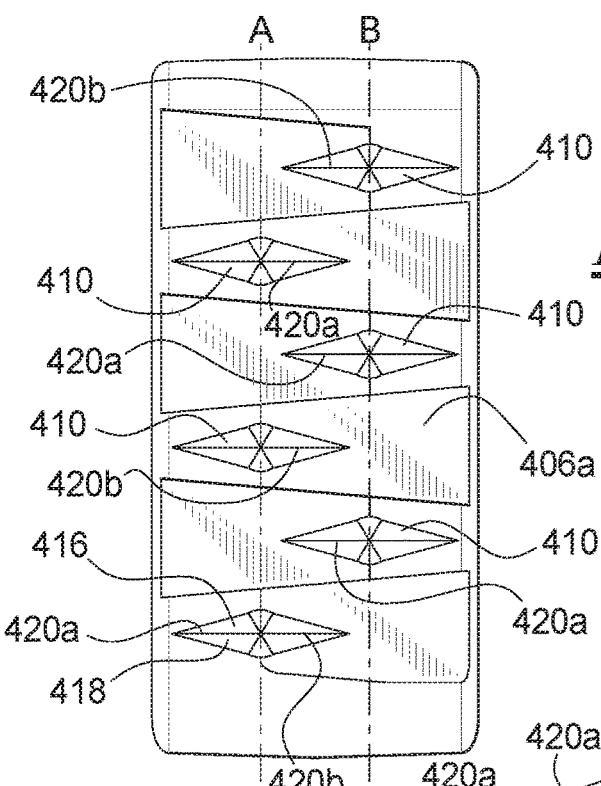
FIGS. 48-52 are enlarged views of an embodiment of a tube retaining surface that could be used on a tube holder.
Figure 49:
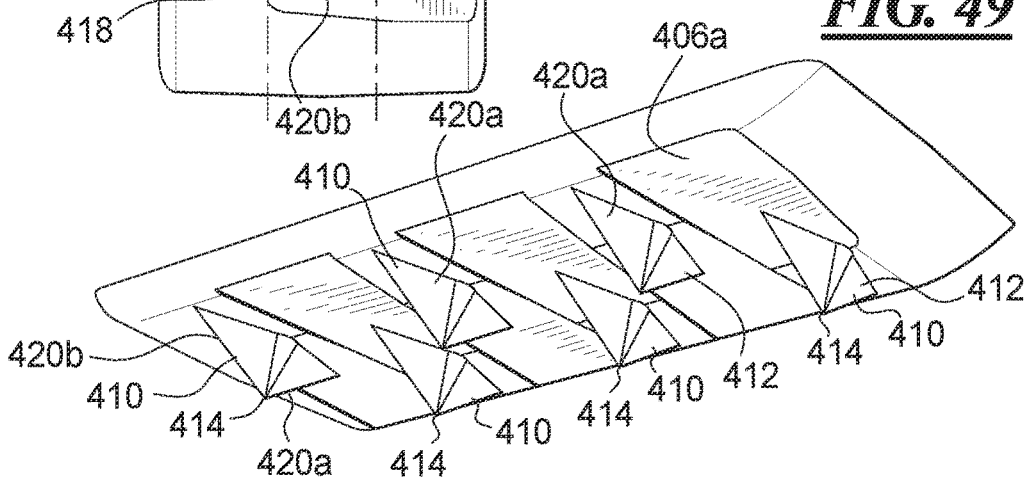
Figure 50:
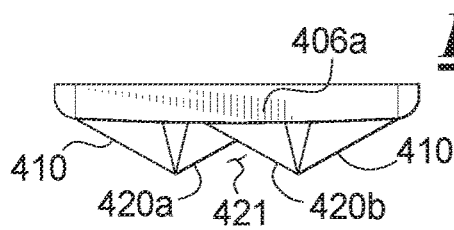
Figure 51:
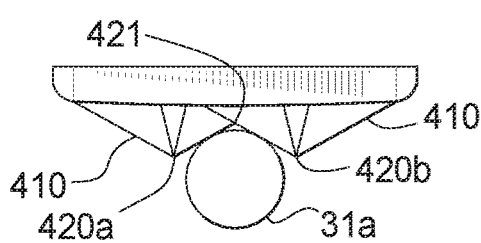
Figure 52:
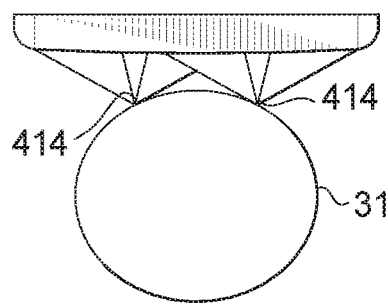

Optionally, the tube holder 334 may also include a securing element to hold the housing 336 in the closed position. Referring to FIGS. 37, 38 and 43, in the illustrated embodiment, the securing element is a flexible strap 368. At one end of the strap 368 is a tongue or free end 370 and at the other end is an enlarged stop or retaining portion 372. Referring to FIGS. 37 and 42, the upstanding wall 366 of the bottom portion includes an opening 374 for receiving the strap 368. During assembly and prior to distribution to the user, the tongue 370 may be inserted and feed through the opening 374 the upstanding wall 366 of the bottom portion 344 of housing 336, wherein the enlarged retaining portion 372 abuts the edges of the opening to secure the strap 368 to the bottom portion 344.

Referring to FIGS. 37-39 and 41, the top portion 344 of the housing 336 includes a strap clamping member 378 for securing a portion of the strap 368 to the top portion 346 of the housing 336. The clamping member 378 includes a closed or clamping position wherein a segment of the strap 368 is secured within the clamping member 378. In the illustrated embodiment, the clamping member 378 includes a movable arm or elongated lever 380 that has a free end 382 and an end 384 that is hingedly connected to the top portion 346 of the housing 366. The hinge 386 may be any suitable hinge, such as a piano hinge or a living hinge. The arm 380 includes an elongated boss or axial rib 388 which protrudes from the arm 380 and is received into a well 391 (FIG. 41) in the top portion 346 of the housing when the arm 380 is moved into the clamped position. The arm 380 is locked into the clamped position by the free end 382 engaging a catch 390 in the top portion 346. In the illustrated embodiment, the catch 390 includes an angled or slanted surface 392 (FIG. 39). When the arm 380 of the clamp is closed, the free end 382 of the arm engages and slides past the angled surface 392 and moves to a position under catch 390. A tab 394 for releasing the clamping member 378 extends outwardly from the catch 390. To release the clamping member 378, the medical professional presses down on the tab 394 to move the catch 390 upward and allow the free end 382 of the arm 380 to pass thereby. Optionally, a second tab 396 may be located beneath the first tab 394 so that the user may push the tabs together to move the catch 390 to the opened or release position.

In use, the housing 366 is opened and an ET tube is placed in the passageway 338 of the housing. The housing 336 is then closed and the strap 368 is placed between the arm 380 and the well 391 in the top portion 346 of the housing 336. Optionally, the strap 368 is pulled and held to remove slack. The strap 368 may be textured with, for example, ribs 398 for gripping the strap. The arm 380 is then moved downward and the boss 388 contacts the strap 368. As the arm 380 is moved downward and the boss 388 is moved into the well 391, the boss 388 pushes a portion of the strap 368 into the well 391. The arm 380 is moved until the free end 382 of the arm moves past the catch 390 and is positioned thereunder, thereby locking the arm in place to clamp and hold the strap in place. To open the clamping member 378, the tab 394 is pushed downward, thereby moving the catch 390 and allowing the arm 380 to be moved upward. The housing 366 may then be opened to adjust or remove the ET tube.

FIGS. 44-47 illustrate another embodiment of a tube holder 400 that includes a body 402 and a retaining member, such as strap 404. In this embodiment, an ET tube is held in position between the bottom surface 406 of body 402 and the strap 404.

Turning first to the body 402, the bottom surface 406 of the body 402 may include a textured surface for contacting a tube. In the illustrated embodiment, the bottom surface 406 includes protrusions or spikes 408 that contact the tube. FIGS. 48-52 illustrate a bottom surface 406a that includes a plurality of protrusions or spikes 410 which may have a wedged or shark-tooth shaped configuration. The protrusions 410 may have a generally triangular shape including an elongated base 412 and a peak 414. The protrusions 410 have at least a front side 416 and a back side 418 which meet at opposed edges 420a and 420b. Furthermore, the protrusions may be configured into a first row and a second row wherein the peaks 414 of the protrusions in the first row are aligned along an axis A and the peaks 414 of the protrusions of the second row are aligned along an axis B, which is offside from the axis A. In other words, the first and second rows may be offset from one another. Furthermore, the edges 420a and 420b of the protrusions may be located between axis A and axis B. In one embodiment, the edges of the protrusions of each of the rows overlap so as to define a passageway configured to accept a tube.

The protrusions 410 of bottom surface 406a may be particularly useful for holding tubes of different sizes. For example, referring to FIG. 52, when a larger tube 31 is held, the larger tube may be contacted by the peaks 414 of the protrusions 410. When a smaller tube 31a is held, referring to FIGS. 50 and 51, the smaller tube 31a may be located in the passageway 421 defined by the overlapping edges 420a and 420b of each row and in contact with the edges to hold the tube. The bottom surface 406a, the shark-tooth shaped protrusions 410 and the layout of the protrusions may be used with any of the tube holders disclosed herein or any other tube holder having a surface contacting a tube. For example, in one embodiment, the plurality of protrusions define at least a first row and a second row, wherein the protrusions have peaks and bases and the at least first and second rows are spaced apart such that the peaks are configured to contact a larger endotracheal tube and the bases are configured to contact a smaller endotracheal tube. The peaks may be configured to contact larger tubes having a size of about 6 mm-10 mm, as they are commonly referred to in the field. The bases may be configured to contact a smaller tube having a size of about 3 mm-8 mm, as they are commonly referred to in the field.

Turning back to FIGS. 44-47, the body 402 defines on one side thereof, an elongated passageway 422 (FIGS. 45 and 46) for accepting and holding strap 404. In the illustrated embodiment, the body 402 includes an appendage 424 defining the elongated passageway 422 and having a slit 428. The enlarged end 431 of the strap 404 (FIGS. 44 and 47) is inserted into the elongated passageway 422 and the strap extends from the slit 428. The body 402 also includes a strap clamping member 430, similar to the one described earlier, for clamping and holding the strap 404. The clamping member 430 includes a closed or clamping position wherein a segment of the strap 404 is secured within the clamping member. In the illustrated embodiment, the clamping member 430 includes a movable arm or clamping lever 432 that has a free end 434 and an end 436 (FIG. 46) that is hingedly connected to the body 402. The hinge 438 may be any suitable hinge, such as a piano hinge or a living hinge. The arm 432 includes an elongated boss or axial rib 440 which is received into a well 442 (FIG. 46) in the body 402 when the arm 432 is moved into the clamped position. The arm 432 is locked into the clamped position by the free end 434 engaging a catch 444. In the illustrated embodiment, the catch 444 includes an angled or slanted surface. When the arm 432 of the clamp is closed, the free end 434 of the arm engages and slides past the angled surface and moves to a position under catch 444. A tab 448 for releasing the clamping member 430 extends outwardly from the catch 444. To release the clamping member 430, the medical professional presses down on the tab 448 to move the catch 444 upward and allow the free end 434 of the arm 432 to pass thereby.

In use, a tube is placed against the bottom surface 406 of body 402. The strap 404 is then wrapped around the tube. The portion of the strap 404 contacting the tube may be textured to aid holding the tube. For example, the strap 404 may include longitudinal extending ribs 450 (FIG. 47) that extend parallel to the longitudinal axis of the strap. The strap 404 is placed between the arm 432 of the clamping member and the well 442. Optionally, the strap 404 is pulled and held to remove slack. The strap 404 may be textured with, for example, ribs 452 (FIG. 47) for gripping the strap. The arm 432 is then moved downward and the boss 440 contacts a segment of the strap 404. As the arm 432 is moved downward and the boss 440 is moved into the well 442, the boss 440 pushes a portion of the strap 440 into the well 442. The arm 432 is moved until the free end 434 of the arm moves past the catch 444 and is positioned thereunder, thereby locking the arm in place to clamp the strap. To open the clamp, the tab 448 is pushed downward, thereby moving the catch 444 and allowing the arm 432 to be moved upward.

Figure 53:
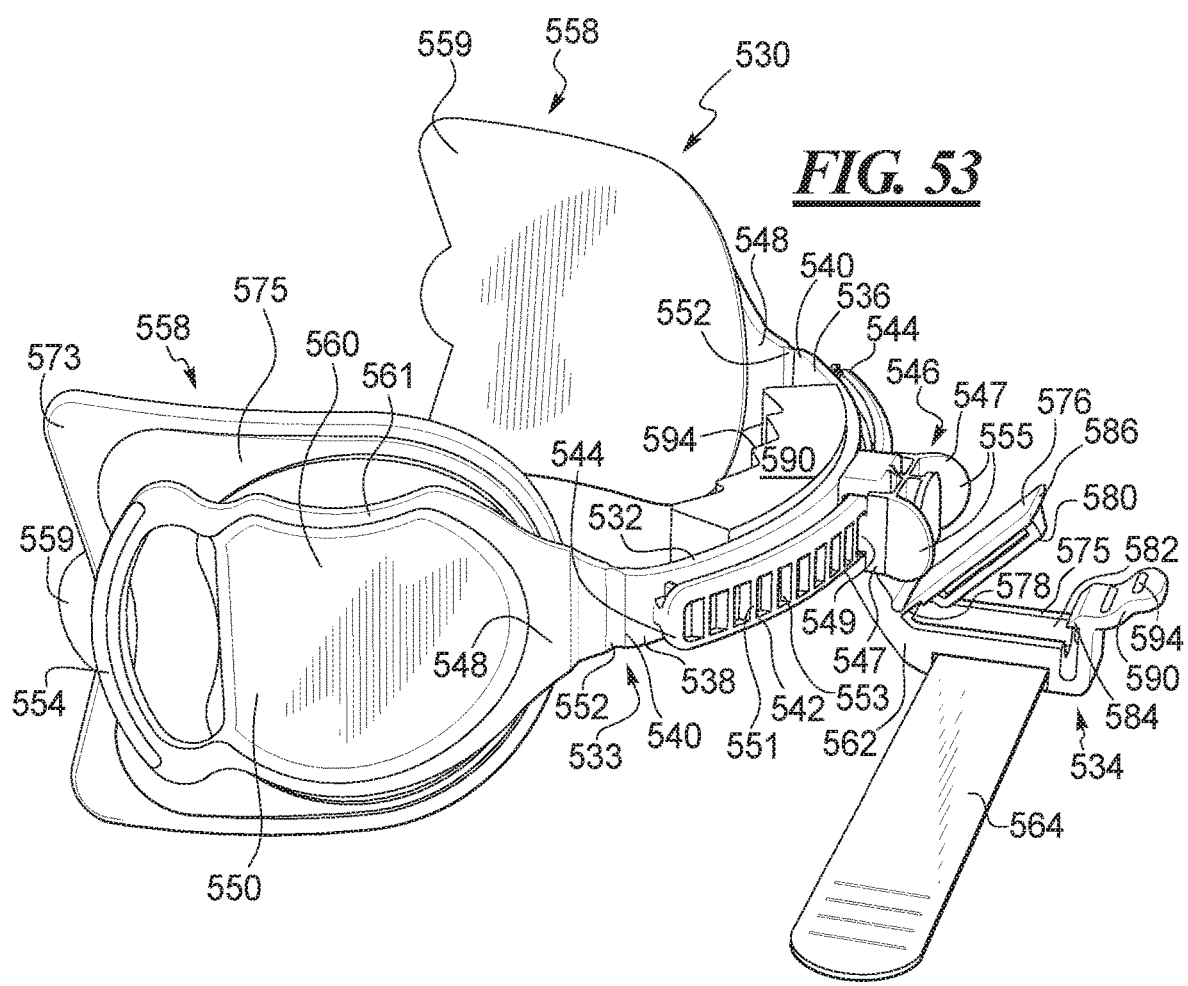
FIG. 53 is a perspective view of another embodiment of an ET tube holding device of the present disclosure.
Figure 54:
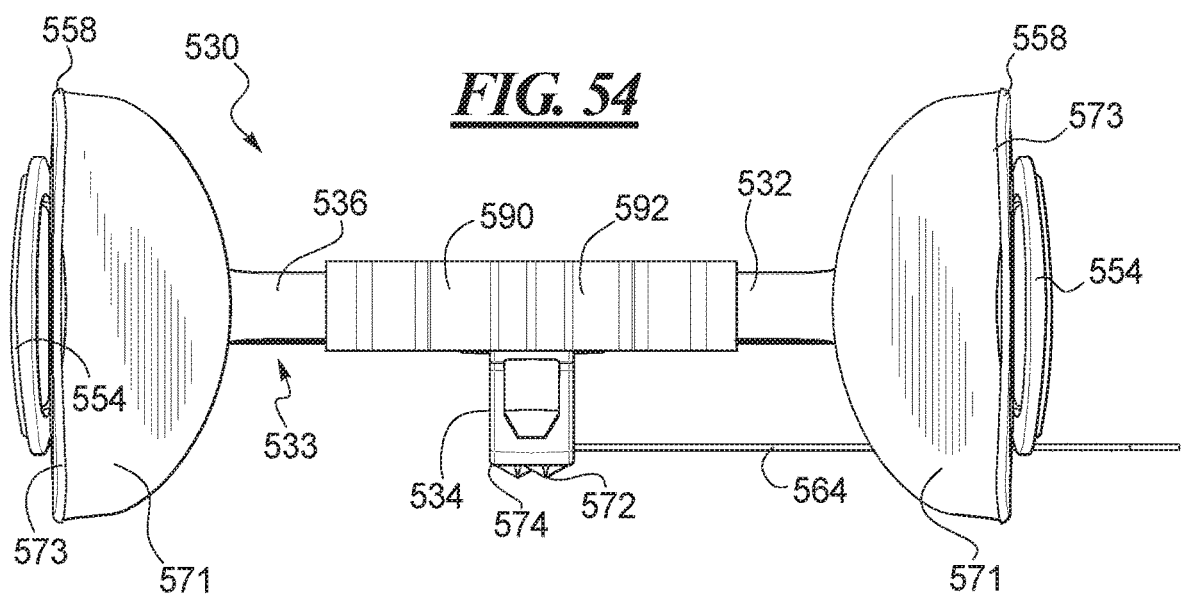
FIG. 54 is a rear elevation view of the ET tube holding device of FIG. 53.

FIGS. 53-55 illustrate another embodiment of a device 530 for holding and securing a tube (not shown), such as an ET tube, on a patient. As with the other embodiments disclosed herein, the features of device 530 may be combined with features of the other exemplary devices described above, and the features of the devices described above may be combined with device 530. For example, any of the rail designs, tube holders, positioning members, frames, etc. described herein may be mixed and matched or combined to form a tube holding and securing device.

Device 530 generally includes a frame 533 that has an elongated central support or elongated central beam 532 which is configured to fit adjacent to a lip on a patient's face and support a tube holder 534. In this example, the beam 532 is configured to rest above the patient's upper lip. However, the beam 532 can also be configured to rest below a patient's lower lip in another example. In each example, however, the beam 532 is intended to extend laterally or lie horizontally across a portion of the patient's face and support or carry the tube holder 534. The beam 532 has an inner side 536 that faces a patient's face and an exposed side 538 opposite the inner side 536. The beam 532 also has a pair of opposite ends 540.

The beam 532 may also have a rail 542 to which the tube holder 534 may be coupled or mounted. In the illustrated embodiment, the tube holder 534 is slidably mounted to rail 542 so as to be slidable along the rail 542 and preferably slidable along the rail 542 between the opposite ends 544 thereof. In other embodiments, the tube holder 534 may be non-slidably attached to beam 532. When the tube holder 534 is slidably mounted on rail 542, the device 530 may further include a positioning member 546 that allows selective lateral repositioning of the tube holder 534, as well as the ET tube that is held or secured thereby, along the rail 542. The positioning member 546 may be releasably locked into position relative to rail 542 to allow selectively repositioning thereof. The positioning member 546 is configured to retain the tube holder 534 at a selected position along the rail 542 until the positioning member 546 is unlocked to allow movement thereof along the rail 542. The rail 542 and positioning member 546 may have any suitable configuration that allows the positioning member 546 to be repositioned along the rail 542, such as that shown in FIGS. 8-14 or the configuration described in the above mentioned US Pub. Pat. Application No. 2014/0261462, which is hereby incorporated herein by reference.

In the illustrated embodiment, referring to FIGS. 53 and 56, the positioning member 546 has a locking mechanism that includes a pair of dogs or flex fingers 547 oriented generally perpendicular to the rail 542. The flex fingers 547 are resiliently connected to the positioning member 546 and have prongs 549 that project rearward toward the rail 542. The prongs 549 are positioned to engage any one of a plurality of ratchet teeth 551 provided on a front face of the rail 542. When the flex fingers 547 are in an unflexed condition, the prongs 549 seat in recesses 553 between the teeth 551. Grip ends 555 on the flex fingers 547 can be squeezed together, which spreads the flex fingers outward away from one another and disengages the prongs 549 from the ratchet teeth 551. When the prongs 549 are disengaged, the positioning member 546 can slide along the rail 542 to a desired position. When pressure on the grip ends 555 the flex fingers 547 is released, the prongs 549 will return and engage the ratchet teeth 551 to retain the positioning member 546 in the selected position along the rail 542.

The beam 532 and/or rail 542 may be made of a tough, durable, semi-rigid, flexible, or very flexible material, such as polyethylene or polyurethane, and may be preformed or molded with a curved or arcuate shape to fit on a region of the patient's face adjacent to and along one lip of the patient. The beam 532 may have a length of between about 30 mm and about 60 mm. In one embodiment, the beam 532 may be designed to fit the smaller face of a pediatric or petite patient and may have a length of between about 30 mm and about 55 mm. For adult patients, the beam may have a length between about 50 mm and about 60 mm.

Referring still to FIGS. 53 and 56, the tube holder 534 has an arm 562 that extends in a direction perpendicular to the rail 542 and in a direction away from the exposed or outer surface 538 of the beam 532. The tube holder 534 includes an elongate tube strap 564 of an elastomeric material, which is similar to the tube strap shown in FIG. 47. As shown in FIG. 56, a slot 568 for receiving the tube strap 564 is formed across the arm 562. The slot 568 may have chamfered or recessed entries 570 on either side so that the strap 564 can be threaded through the slot in either direction and an enlarged retaining portion (similar to the enlarged retaining portion 431 shown in FIG. 47) can seat in one of the chamfered entries 570, fixing that end of the strap to the arm 562. A free length of the tube strap 564 extends in a direction transverse to arm 562 and can be wrapped around the ET tube. An adhesive pad or layer (not shown), such as a suitable pressure-sensitive adhesive, can be provided on an inner surface of the tube strap 564 to further restrain the ET from rotational or longitudinal movement when secured against the bottom of the arm 562. A plurality of sharp, nub-like tangs or spikes 572 can also be provided on the bottom surface 574 of the arm 562. The spikes 572 can impinge on and/or otherwise engage the exterior surface of the ET tube to frictionally and/or physically engage the ET tube and further restraining the tube from movement. In one embodiment, the bottom surface 574 may have the configuration shown in FIGS. 48-52, such the tube holder may be able to hold both adult and pediatric sized tubes.

Referring back to FIGS. 53 and 56, a clamping mechanism is provided on a top side 575 of the arm 562, opposite the bottom side 574. The clamping mechanism in this example is substantially similar to that disclosed in the aforementioned '462 published patent application. The clamping mechanism may be any suitable mechanism or member that is configured to securely engage and clamp a segment of the tube strap 564 along its free length. The clamping mechanism can maintain the tube strap 564 in tension to further help restrain the ET tube from unintended movement. In the disclosed example, the clamping mechanism is an elongate, cantilevered clamping lever 576 that is attached via a living hinge 578 to the tube holder 534. The clamping lever 576 can be pivoted and raised about the living hinge 578. The free length of the tube strap 564 can be folded over the top side 575 of the arm 562. The clamping lever 576 can be lowered and locked in place against the arm 562 to pinch and maintain the tube strap 564 in tension about the ET tube. A lengthwise or axial rib 580 is provided in this example and protrudes down from the clamping lever 576. The top side 575 of the arm 562 has a corresponding longitudinal or lengthwise channel or recess 582 (FIG. 53) sized to receive the rib 580 when the clamping lever is closed. The rib 580 and channel 582 are provided in order to crimp the tube strap 564 and aids in preventing the tube strap from slipping from between the arm 562 and the clamping lever 576.

In this embodiment, a latching mechanism is also provided to lock and hold the clamping lever 576 in the locked or clamped condition. The latching mechanism in one example can have a flexible, resilient catch 584 provided on the top side 575 and near the front end of the arm 562. When the clamping lever 576 is lowered onto the top side 575 of the arm 562, the catch 584 will flex forward to permit the front edge 586 of the clamping lever 576 to snap past the catch 584. The catch 584 then holds and retains the clamping lever 576 in the closed or clamped position to tightly engage the tube strap 564. To release the ET tube, a person can pull the catch 584 forward and/or upward at an angle away from the clamping lever 576 until the front edge 586 can clear the catch 584. The clamping lever 576 can then be raised to release the tube strap 564. This type of latching mechanism allows one to release the ET tube, readjust its position, and then re-secure the tube again without having to replace any components, tape, and the like. In this embodiment, the catch 584 includes a release tab 590 extending outwardly in a direction perpendicular to the beam 532. The release tab 590 serves as a lever that when pressed, moves the catch 584 to allow the front edge 586 of the clamping lever 576 to clear the catch 584, thereby opening the latching mechanism. In the illustrated embodiment, the release tab 590 may have a stepped configuration and/or angled configuration, such as the S-shaped configuration shown in FIG. 56 or a Z-shaped configuration. The end portion 592 of the release tab 590 may be offset from or above the catch 584 in that the tab may be offset or above the plane from which the tab resides. Furthermore the release tab 590 may be textured to assist in the user in gripping the tab. For example, the release tab 590 may include protrusions 594. This configuration provides a gripping surface and leverage to assist the user in moving the catch 584. As will be evident to those having ordinary skill in the art upon reading this disclosure, the disclosed device 530 is not to be limited to the particular tube holder construction disclosed herein. The arm, latching means, clamping means, flexible leg, and positioning member can vary in configuration and construction and yet function as intended.

Turning to FIGS. 53-55, extending from each end 540 of beam 532 is an arm 548 that has a cheek plate 550 at or adjacent to free end thereof. Between each arm 548 and the end 540 of the beam 532 is a hinge 552, such as the living hinge shown. The hinges 552 allow the frame 533 to accommodate difference sized faces and swelling of the patient's face, when such swelling occurs. The hinges 552 also allow the arms 548 to be folded inward so as to place the frame 533 in a compact configuration for storage and distribution. This is particularly useful for individuals that are required to carry light trauma packs, such as first responders and military personnel.

The cheek plates 550 may be curved or contoured to closely follow the curved contour of a patient's face. In the illustrated embodiment, the cheek plates 550 have a generally arcuate portion 560 (FIG. 53), which may be in the shape of a circle, oval or ellipse. Furthermore, the arcuate portion 560 of the cheek plates 550 may have a continuous surface with no openings or breaks. Additionally, the arcuate portion 560 of the cheek plates 550 may include an indicator that indicates the orientation of the device 530. For example, the arcuate portion 560 may have an indent or cutout 561 that provides a visual indication of the top of device 530. This may be useful during manufacturing of the device and/or use of the device during an emergency situation. Also, each cheek plate 550 in this example can have one or more strap loops 554 at or near their free ends. An adjustable head/neck strap, such as any of those disclosed herein or any other suitable head/neck strap, can be coupled to the frame 533 of device 530 via the strap loops 554 for securing the device 530 to a patient's head and aid in retaining the frame 533 on the patient's face.

Referring to FIGS. 53-55 and 57, a skin friendly cheek pad 558 may also be coupled to each of the cheek plates 550 on the inside face of each plate. The cheek pad may be coupled to the cheek place by gluing or welding. The cheek pads 558 may cover and/or extend beyond the cheek plates 550, including the strap loops 554. For example, in the illustrated embodiment, the ends 579 of the cheek pads 558 extend beyond the strap loops 554. This may assist in reducing any discomfort or irritation to the patient caused by the cheek plates rubbing or contacting the patients skin.

The cheek pads 558 may be formed of a skin friendly adhesive or a skin friendly adhesive layer may be provided on the face contacting side 571 (FIG. 54) of each of the cheek pads 558. A release liner 559 may cover the adhesive until just prior to use. The cheek pad 558 can help adhere the cheek plates 550 to the patient's face during use. In one embodiment, the outer portion 573 of the cheek pads 558, including the outer edges, optionally, can be tapered in that the outer portions 573 of the cheek pads 558 are thinner than toward the center 575 of the cheek pads 558. In other words, the center 575 may be thicker than the outer portions 573 wherein the cheek pads taper outwardly. The tapering could be graduated in that the thickness of the adhesive layer gradually becomes thinner toward the outer portion. In other embodiments the thickness could change step-wise. Tapering allows the cheek pad 558 to be more flexible at the outer portions 573. The more flexible outer portions 573 may provide benefits. For example, when the cheek pads 558 extend beyond the strap loops 554 of the cheek plates 550, as shown in FIGS. 53-55, the thinner more flexible outer portions 573 of the cheek pads 558 allows the user to bend the outer portions 573 during attachment and adjustment of the head/neck straps to the strap loops 554. Also the flexible outer portions may aid in allowing the cheek pad 558 to better conform to the patient's face.

The device 530 may also include a separate lip pad 590 provided on the inner side 536 of the beam 532. The lip pad may be any of those disclosed herein or any other suitable lip pad. In the illustrated embodiment, the lip pad 590 includes an inner surface 592 having three or more contact points for contacting the patients lip or skin between the lip and nose. For example, the illustrated lip pad 590 includes a wavy profile as viewed from the top (FIG. 55) wherein the inner surface 592 includes three or more protrusions 594 that are configured to contact the patient. Having multiple points of contact may reduce the pressure applied to the patients face, thus reducing discomfort to the patient.

As will be evident to those having ordinary skill in the art, the beam, cheek plates, cheek pads, tube holder and head strap can vary in configuration and construction and yet fall within the scope of the invention and claims. The beam and cheek plates can be molded as one integrated plastic structure, if desired. The head strap can be formed having any suitable adjustable fastening mechanism, such as a hook and loop structure on a fabric strap. The cheek plates can be formed to have any number of configurations and constructions and can utilize a minimum amount of base material (i.e., plastic) and yet function as intended.

As shown from the above description, the present invention has several different aspects, which are not limited to the specific structures shown in the attached drawings and which do not necessarily need to be used together. Variations of these concepts or structures may be embodied in other structures without departing from the present invention as set forth in the appended claims.

What is claimed is:

1. A device for holding an endotracheal tube to a patient, the device comprising:
    a support configured to fit adjacent to a patient's mouth;
    a tube holder configured to hold an endotracheal tube wherein the tube holder is coupled to the support, the tube holder comprising:
        a body having opposed sides and a bottom side, the bottom side having a plurality of shark-tooth shaped protrusions for contacting the endotracheal tube, the shark-tooth shaped protrusions having a front surface and a back surface that meet to define a side edge;
        the plurality of shark-tooth protrusions comprising a first row of protrusions offset from a second row of protrusions, wherein the shark-tooth protrusions in the first row of protrusions include peaks that are along a first axis and the shark-tooth protrusions in the second row of protrusions include peaks along a second axis offset from the first axis, the shark-tooth protrusions of the first and second rows having an alternating configuration wherein the shark-tooth protrusions of the first row are longitudinally staggered relative to the shark-tooth protrusions of the second row;
        wherein the side edges of the shark-tooth protrusions in the first row of protrusions and the side edges of the shark-tooth protrusions in the second row of protrusions are located between the first axis and second axis, and the side edges of the shark-tooth protrusions in the first row overlap the shark-tooth protrusions in the second rows in a third axis that is parallel to the first and second axis; and
        an elongated, flexible strap extending from one side of the body and having a free length adapted to be wrapped around the bottom side of the body and the endotracheal tube to secure the endotracheal tube to the bottom side of the body.

2. The device of claim 1 wherein the overlapping side edges of the protrusions of the first and second rows define a passageway for receiving the endotracheal tube.

3. The device of claim 1 wherein a passageway for receiving the endotracheal tube is defined between the first and second rows of protrusions.

4. The device of claim 1 wherein the support is elongated and the device further includes a positioning member slidably mounted to the elongated support and coupling the tube holder to said elongated support, the positioning member being selectively laterally repositionable along the elongated support so as to reposition the tube holder relative thereto, the positioning member being releasably lockable in position relative to the elongated support.

5. The device of claim 1 wherein the support includes opposed ends and a first arm extending from one of the opposed ends of the support and a second arm extending from the other of the opposed ends of the support.

6. The device of claim 5 further including a two-piece strap for securing the support to the patient's head, wherein the two-piece strap is configured to encircle a patient's head or neck and be connected to the arms, the two-piece strap including a first elongated segment having first and second end portions and a second elongated segment having first and second end portions, the first end portion of the first elongated segment being adapted to be adjustably connected to the first arm and the second end portion of the second elongated segment being adapted to being adjustably connected to the second arm, the second end portion of the first elongated segment and the first end portion of the second elongated segment being releasable connected to each other to allow adjusting of the strap.

7. The device of claim 6 wherein the first segment is longer in length than the second segment.

8. The device of claim 6 wherein one of the second end of the first segment and the first end of the second segment include hook material and the other the second end of the first segment and the first end of the second segment include loop material.

9. The device of claim 5 wherein the first arm includes a first cheek plate and the second arm includes a second cheek plate, wherein each of the first and second cheek plates include a cheek pad.

10. The device of claim 9 wherein each of the cheek pads is configured to prevent the respective cheek plate from contacting skin of a user.

11. The device of claim 9 wherein each of the cheek pads substantially covers the entire respective cheek plate.

12. The device of claim 9 wherein each of the cheek pads extends beyond an end of the respective cheek plate.

13. The device of claim 1 wherein the tube holder includes a clamping mechanism for clamping the strap to the tube holder.

14. The device of claim 13 wherein the clamping mechanism includes a lever for clamping the strap to the tube holder.

15. The device of claim 14 wherein the clamping mechanism further includes a catch for retaining the clamping lever.

16. The device of claim 15 further including a release tab for moving the catch wherein the release tab has a general S-shape or Z-shape configuration.

17. The device of claim 15 further including a release tab for moving the catch wherein the release tab has a general stepped configuration.

* * * * *